(12) United States Patent
Lowet et al.

(10) Patent No.: US 11,484,261 B2
(45) Date of Patent: Nov. 1, 2022

(54) DYNAMIC WEARABLE DEVICE BEHAVIOR BASED ON SCHEDULE DETECTION

(71) Applicant: KONINKLIJKE PHILIPS N.V., Eindhoven (NL)

(72) Inventors: Dietwig Jos Clement Lowet, Eindhoven (NL); John Cronin, Bonita Springs, FL (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/537,716

(22) PCT Filed: Dec. 18, 2015

(86) PCT No.: PCT/EP2015/080676
§ 371 (c)(1),
(2) Date: Jun. 19, 2017

(87) PCT Pub. No.: WO2016/097381
PCT Pub. Date: Jun. 23, 2016

(65) Prior Publication Data
US 2018/0000414 A1    Jan. 4, 2018

Related U.S. Application Data

(60) Provisional application No. 62/094,885, filed on Dec. 19, 2014.

(30) Foreign Application Priority Data

Jun. 29, 2015   (EP) .................................... 15174337

(51) Int. Cl.
*A61B 5/00* (2006.01)
*A61B 5/0205* (2006.01)
(Continued)

(52) U.S. Cl.
CPC .............. *A61B 5/6802* (2013.01); *A61B 5/00* (2013.01); *A61B 5/02055* (2013.01);
(Continued)

(58) Field of Classification Search
CPC ..... A61B 5/6802; A61B 5/00; A61B 5/02055; A61B 5/1112; A61B 5/1118; A61B 5/165;
(Continued)

(56) References Cited

U.S. PATENT DOCUMENTS

| | | | |
|---|---|---|---|
| 5,738,104 A * | 4/1998 | Lo ........................ | A61B 5/7203 600/509 |
| 6,876,947 B1 * | 4/2005 | Darley .................. | A61B 5/1118 702/144 |

(Continued)

FOREIGN PATENT DOCUMENTS

| | | | |
|---|---|---|---|
| JP | 2006320735 A | 11/2006 | |
| JP | 2010146223 A | 7/2010 | |

(Continued)

OTHER PUBLICATIONS

Windau, et al., "Situation awareness via sensor-equipped eyeglasses", 2013 IEEE/RJS International Conference on Intelligent Robots and Systems (IROS), Nov. 3, 2013, Tokyo, Japan, pp. 5674-5679.

*Primary Examiner* — Carl H Layno
*Assistant Examiner* — Michael J Lau

(57) ABSTRACT

Various embodiments described herein relate to a method and related wearable device and non-transitory machine-readable medium including receiving sensor data from at least one sensor of the wearable device; comparing the sensor data to schedule format stored in a memory of the wearable device, wherein the schedule format specifies at least one characteristic of sensor readings previously associated with a predefined context; determining that the
(Continued)

received sensor data matches the schedule format; determining, based on the received sensor data matching the schedule format, that the user is currently in the predefined context; identifying an action associated with the predefined context; and executing the action while the user is in the predefined context.

18 Claims, 17 Drawing Sheets

(51) Int. Cl.
    *A61B 5/11*                   (2006.01)
    *G06F 1/16*                   (2006.01)
    *G06Q 10/10*                 (2012.01)
    *G06Q 10/06*                 (2012.01)
    *A61B 5/16*                   (2006.01)

(52) U.S. Cl.
    CPC ........... *A61B 5/1112* (2013.01); *A61B 5/1118* (2013.01); *A61B 5/7271* (2013.01); *A61B 5/7435* (2013.01); *G06F 1/163* (2013.01); *G06Q 10/06314* (2013.01); *G06Q 10/10* (2013.01); *A61B 5/165* (2013.01); *A61B 5/7267* (2013.01); *A61B 5/74* (2013.01); *A61B 5/7455* (2013.01)

(58) Field of Classification Search
    CPC ....... A61B 5/7267; A61B 5/74; A61B 5/7455; G06F 19/00; G06F 1/163; G06Q 10/10; G06Q 10/06314
    USPC ........................................................ 600/301
    See application file for complete search history.

(56) References Cited

U.S. PATENT DOCUMENTS

| | | | |
|---|---|---|---|
| 7,704,211 B1* | 4/2010 | Koh | A61B 5/14551 600/300 |
| 8,021,297 B2* | 9/2011 | Aerts | A61B 5/222 600/300 |
| 2001/0049471 A1 | 12/2001 | Suzuki et al. | |
| 2003/0227386 A1* | 12/2003 | Pulkkinen | A61B 5/1127 340/8.1 |
| 2004/0116837 A1* | 6/2004 | Yamaguchi | A63B 69/0028 600/595 |
| 2005/0149136 A1* | 7/2005 | Siejko | A61B 5/4836 607/17 |
| 2006/0004680 A1* | 1/2006 | Robarts | G06F 16/40 706/46 |
| 2009/0105560 A1* | 4/2009 | Solomon | G16H 40/67 600/301 |
| 2009/0216141 A1* | 8/2009 | Fischell | A61B 5/0031 600/509 |
| 2009/0276013 A1* | 11/2009 | Matos | G16H 40/63 128/903 |
| 2009/0292222 A1* | 11/2009 | Ferren | A61B 5/4818 600/549 |
| 2010/0138379 A1* | 6/2010 | Mott | G06N 5/02 706/52 |
| 2010/0160745 A1* | 6/2010 | Hills | A61B 5/4238 600/549 |
| 2011/0193704 A1* | 8/2011 | Harper | A61B 5/7282 340/573.1 |
| 2011/0267196 A1* | 11/2011 | Hu | A61B 5/0002 340/575 |
| 2011/0319725 A1* | 12/2011 | Tsurumoto | A61B 5/0002 600/301 |
| 2012/0023135 A1* | 1/2012 | Dahlkvist | G06Q 10/10 707/E17.023 |
| 2012/0029361 A1* | 2/2012 | Addison | A61B 5/02125 600/484 |
| 2012/0172684 A1* | 7/2012 | Buchheim | A61B 5/02438 600/301 |
| 2012/0238800 A1* | 9/2012 | Naujokat | A61B 5/318 600/26 |
| 2013/0012836 A1* | 1/2013 | Crespo Veiga | A61B 5/725 600/595 |
| 2013/0023739 A1* | 1/2013 | Russell | G16H 40/63 600/301 |
| 2013/0109997 A1* | 5/2013 | Linke | A61B 5/0008 600/300 |
| 2013/0344851 A1 | 12/2013 | Brdiczka et al. | |
| 2014/0012511 A1* | 1/2014 | Mensinger | A61B 5/4839 702/19 |
| 2014/0018635 A1* | 1/2014 | Buchheim | A61B 5/7221 600/301 |
| 2014/0030684 A1* | 1/2014 | Steinmetz | A61B 3/10 600/323 |
| 2014/0039383 A1* | 2/2014 | Dobbles | A61M 15/0068 604/66 |
| 2014/0039839 A1* | 2/2014 | Yuen | A61B 5/6838 702/189 |
| 2014/0052681 A1* | 2/2014 | Nitz | G06N 5/046 706/46 |
| 2014/0066703 A1* | 3/2014 | Blumenkranz | A61B 90/30 600/114 |
| 2014/0067096 A1* | 3/2014 | Aibara | G06Q 10/0639 700/91 |
| 2014/0073486 A1* | 3/2014 | Ahmed | A61B 5/1112 600/479 |
| 2014/0121540 A1* | 5/2014 | Raskin | G16H 40/63 600/479 |
| 2014/0129178 A1* | 5/2014 | Meduna | G06F 3/017 702/189 |
| 2014/0156084 A1* | 6/2014 | Rahman | G16H 40/67 700/275 |
| 2014/0234815 A1* | 8/2014 | Jang | A61B 5/165 434/236 |
| 2014/0235969 A1* | 8/2014 | Van Der Heide | A61B 5/053 600/407 |
| 2014/0247206 A1 | 9/2014 | Grokop et al. | |
| 2014/0275840 A1* | 9/2014 | Osorio | A61B 5/4094 600/301 |
| 2014/0276163 A1* | 9/2014 | Thakur | A61B 5/7275 600/528 |
| 2014/0334796 A1 | 11/2014 | Galant et al. | |
| 2014/0335490 A1* | 11/2014 | Baarman | A61B 5/1118 434/236 |
| 2014/0336539 A1* | 11/2014 | Torres | A61B 5/162 600/595 |
| 2014/0337451 A1* | 11/2014 | Choudhary | A61B 5/22 709/206 |
| 2014/0343861 A1* | 11/2014 | Edman | A61B 5/4866 702/19 |
| 2014/0358012 A1* | 12/2014 | Richards | H04W 4/027 600/479 |
| 2014/0358473 A1* | 12/2014 | Goel | A61B 5/1118 702/141 |
| 2016/0179197 A1* | 6/2016 | Qian | G06F 1/163 345/156 |

FOREIGN PATENT DOCUMENTS

| | | | | |
|---|---|---|---|---|
| WO | 2014066703 A2 | 5/2014 | | |
| WO | WO 2014066703 A2 * | 5/2014 | ............ | G06F 1/163 |
| WO | WO-2014066703 A2 * | 5/2014 | | |

* cited by examiner

| Context Name | Context Criteria | Sensors | Rules |
|---|---|---|---|
| Home | Schedule Format A | - | - |
| Not Home | Not Schedule Format A | Skin Conductance | B1, B2, B3 |
| Office | Schedule Format B | Blood Pressure, Temperature | A1, A2, A3, A4 |
| Cust. Mtg | Calendar: "Cust. Mtg." | Temperature | C1 |

FIG. 4

| Context | Name | Sensor 1 | Sensor 1 Data | Sensor 2 | Sensor 2 Data | ... | Sensor N | Sensor N Data |
|---|---|---|---|---|---|---|---|---|
| Work | Meeting with Boss | BP | ~ | HR | ~ | | Temp | ~ |
| Exercise | Bike Ride | BP | ~ | HR | ~ | | Speed | ~ |
| Personal | Anniversary Dinner | BP | ~ | HR | ~ | | Temp | ~ |

FIG. 14

DYNAMIC WEARABLE DEVICE BEHAVIOR BASED ON SCHEDULE DETECTION

CROSS-REFERENCE TO PRIOR APPLICATIONS

This application is the U.S. National Phase application under 35 U.S.C. § 371 of International Application No. PCT/EP2015/080676, filed on Dec. 18, 2015, which claims the benefit of European Application No. 15174337.4, filed Jun. 29, 2015 and U.S. Provisional Application Ser. No. 62/094,885, filed Dec. 19, 2014. These applications are hereby incorporated by reference herein, for all purposes.

TECHNICAL FIELD

Various embodiments described herein generally relate to wearable devices, and more specifically, but not exclusively, to the use of wearable devices to trigger actions when a user is engaged in an activity or in a location and to systems and methods for detecting the user's presence in a meeting based on, e.g., movement data and geo-locational data.

DESCRIPTION OF THE RELATED ART

Organizations use information about personnel schedules for many reasons, including: planning, personal assessment, and team assessments. In addition, organizations have taken an interest in coaching personnel, that is, encouraging activities for personal improvement, such as exercise, nutrition, and education. Understanding personnel schedules are useful for providing such coaching.

Furthermore, wearable technology is a new class of electronic systems that can provide data acquisition through a variety of unobtrusive sensors that may be worn by a user. The sensors gather information, for example, about the environment, the user's activity, or the user's health status. However, there are significant challenges related to the coordination, computation, communication, privacy, security, and presentation of the collected data. Additionally, there are challenges related to power management given the current state of battery technology. Furthermore, analysis of the data is needed to make the data gathered by the sensors useful and relevant to end-users. In some cases, additional sources of information may be used to supplement the data gathered by the sensors. The many challenges that wearable technology presents require new designs in hardware and software.

Current wearables permit the tracking of the location of the user wearing the wearable device. Similar systems are used to track workers and assets and ensure that they remain in a desired area.

Organizations typically utilize an individual's calendar appointments (e.g., MS Outlook™) or questionnaires as a source of context information. However, individuals may not maintain their and individuals will often skip meetings. Questionnaires may be time consuming, and therefore organizations may have a low completion rate.

SUMMARY

In general, various aspects of the systems, methods, and apparatus described herein are directed toward deriving context information about individuals' schedules, and more specifically, about their meetings, and using that context information in combination with physiological data gathered from individuals, and to make activity suggestions to users. For example, organizations may use skin conductance and a heart rate sensor as a measure of an individual's stress during meetings.

The context an organization has about personnel schedules in combination with the physiological data collected by sensors provide a measure of which meetings or activities are stressful and which not. In addition, the systems, methods, and apparatus described herein are directed to utilizing geo-locational and movement information to gather contextual information about an individual's meetings.

According to various embodiments, there is a provided a method of determining a user schedule from movement data. The method includes receiving movement data from one or more portable devices; receiving geo-locational data from one or more geo-locational devices; and executing instructions stored in memory. Execution of the instructions by a processor may include determining a location based on the geo-locational data; determining that an idle period exists based on the movement data; determining that a first boundary of the idle period and a second boundary of the idle period correspond to a schedule format; determining a schedule item based on the schedule format; and storing one or more records of the determined location, schedule item, and the user on a tangible computer readable storage medium.

This method provides several advantages for determining context information, including allowing for various applications of the combination of the context information with physiological data measured by sensors, and facilitating activity based recommendations based on a user's schedule and physiological parameters.

In a further embodiment, the one or more portable devices include one or more of a wearable device and a smart phone.

In a further embodiment the method also includes providing an activity alert to a user based on the determined location and schedule item.

In a further embodiment the movement data comprises one or more of step counts, accelerometer data, geo-locational data, and combinations thereof.

In a further embodiment, determining that an idle period exists includes determining that user movement is at or below a defined threshold.

In a further embodiment, the schedule format corresponds to a meeting.

In a further embodiment, the method may further comprise receiving physiological data from body sensors. The physiological data may include one or more of a measure of skin conductance, a measure of blood pressure, a measure of heart rate, a measurement indicating wakefulness, and a measure of skin temperature.

In a further embodiment, the method may further include receiving a calendar event and correlating the schedule item to the calendar event.

According to various embodiments, there is provided a non-transitory computer readable storage medium having embodied thereon a program executable by a processor to perform a method for a user schedule from movement data. The method performed by the processor executing the program includes receiving movement data from one or more portable devices; receiving geo-locational data from one or more geo-locational devices; determining a location based on the geo-locational data; determining that an idle period exists based on the movement data; determining that a first boundary of the idle period and a second boundary of the idle period correspond to a schedule format; determining a schedule item based on the schedule format; and storing one or more records of the schedule item and the user on a tangible computer readable storage medium.

According to various embodiments there is provided a user device for determining a user schedule from movement data. The user device may include a memory configured for receiving movement data from one or more portable data and geo-locational data from one or more geo-locational devices; and a processor configured for executing instructions stored in memory. Execution of the instructions by the processor may include identifying, based on the geo-locational data, a location; identifying, based on the movement data, an idle period; determining that a first boundary of the idle period and a second boundary of the idle period correspond to a schedule format; determining a schedule item based on the schedule format; and storing one or more records of the determined location, schedule item and the user on a tangible computer readable storage medium.

Some preferred embodiments of the disclosure are defined in the dependent claims. It should be understood that the claimed user device and the claimed non-transitory computer readable storage medium can have similar preferred embodiments and the corresponding advantages as the claimed method and as defined in the dependent method claims.

Various embodiments described herein relate to a method for adapting behavior of a wearable device to a user's current context, the method including: receiving sensor data from at least one sensor of the wearable device; comparing the sensor data to schedule format stored in a memory of the wearable device, wherein the schedule format specifies at least one characteristic of sensor readings previously associated with a predefined context; determining that the received sensor data matches the schedule format; determining, based on the received sensor data matching the schedule format, that the user is currently in the predefined context; identifying an action associated with the predefined context; and executing the action while the user is in the predefined context.

Various embodiments described herein relate to a wearable device for adapting behavior to a user's current context, the wearable device including: at least one sensor for receiving sensor data related to a user; a memory storing a schedule format that specifies at least one characteristic of sensor readings previously associated with a predefined context; and a processor in communication with the memory and the at least one sensor, the processor being configured to: compare the sensor data to the schedule format stored in the memory of the wearable device; determine that the received sensor data matches the schedule format; determine, based on the received sensor data matching the schedule format, that the user is currently in the predefined context; identify an action associated with the predefined context; and execute the action while the user is in the predefined context.

Various embodiments described herein relate to a non-transitory machine-readable storage medium encoded with instructions for execution by a processor of a wearable device, the non-transitory machine-readable storage medium including: instructions for receiving sensor data from at least one sensor of the wearable device; instructions for comparing the sensor data to schedule format stored in a memory of the wearable device, wherein the schedule format specifies at least one characteristic of sensor readings previously associated with a predefined context; instructions for determining that the received sensor data matches the schedule format; instructions for determining, based on the received sensor data matching the schedule format, that the user is currently in the predefined context; instructions for identfiying an action associated with the predefined context; and instructions for executing the action while the user is in the predefined context.

Various embodiments are described wherein the action includes activating at least one additional sensor associated with the predefined context, whereby data is collected from the at least one additional sensor while the user is in the predefined context.

Various embodiments are described wherein the action includes activating at least one rule associated with the predefined context, whereby while the user is in the predefined context the rule is periodically evaluated against collected sensor data to determine whether the rule is to be applied.

Various embodiments are described wherein the action includes suppressing delivery of notifications to the user via a user interface of the wearable device.

Various embodiments are described wherein the predefined context is a meeting context and the at least one characteristic identified by the schedule format includes: an first period of relatively high activity; a second period of relatively low activity; and a transition from the first period to the second period at an identified time.

Various embodiments are described wherein the at least one characteristic belongs to a model that is learned by the wearable device based on previous sensor data and previous user feedback.

Various embodiments are described wherein the action includes: determining that the predefined context is associated with a high stress level for the user; and suppressing notifications to the user based on the determinations that the predefined context is associated with a high stress level for the user.

Various embodiments are described wherein the action includes: receiving physiological data from the at least one sensor, wherein the physiological data include one or more of a measure of skin conductance, a measure of blood pressure, a measure of heart rate, a measurement indicating wakefulness, and a measure of skin temperature; and storing the received physiological data in association with the predefined context.

Sensor data may be sensed at a wearable device by one or more sensors, preferably physiological sensors, such as acceleration sensor, heart rate sensor, etc. may be stored in a memory and used by a processor to calculate, e.g., calories burned or weight lost. Raw sensor data may also be used in various embodiments of the present invention, such as a number of steps counted by an acceleration sensor.

The foregoing and other features and advantages of the present invention will be made more apparent from the descriptions, drawings, and claims that follow. One of ordinary skill in the art, based on this disclosure, would understand that other aspects and advantages of the methods, systems, and principles described herein exist.

BRIEF DESCRIPTION OF THE DRAWINGS

In order to better understand various example embodiments, reference is made to the accompanying drawings, wherein:

FIG. 4 illustrates an example wearable database;

FIG. 14 illustrates an example wearable database;

DETAILED DESCRIPTION

Figure 1:
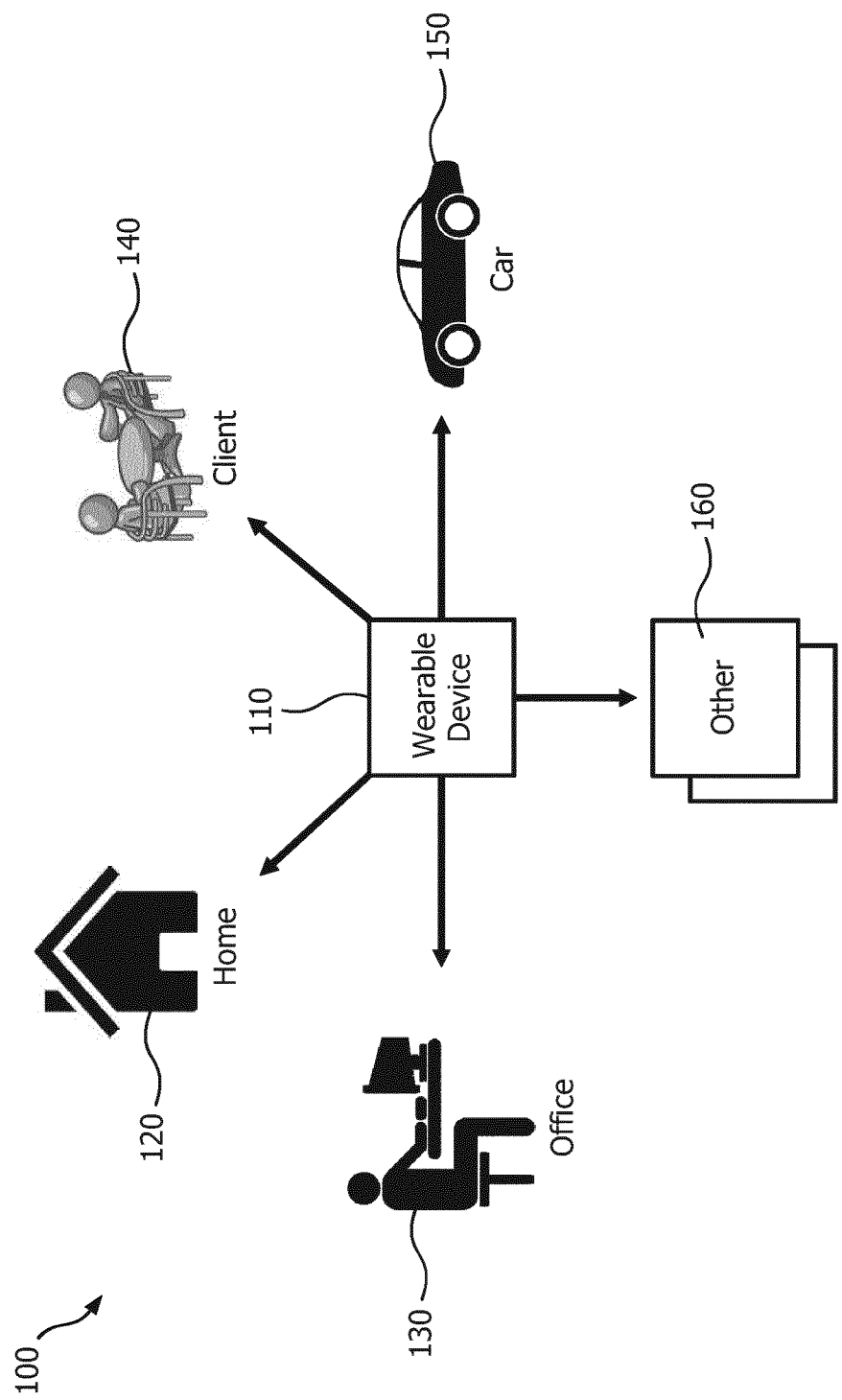
FIG. 1 illustrates an example wearable device that is associated with a plurality of scheduled items and/or activities.

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., or), unless otherwise indicated (e.g., "or else" or "or in the alternative"). Additionally, the various embodiments described herein are not necessarily mutually exclusive and may be combined to produce additional embodiments that incorporate the principles described herein.

Various embodiments described herein include systems and methods wherein movement and geo-locational data is used to generate context information about an individual's schedule items, including meetings. The context information may be used in combination with sensor data from sensors included in a wearable device that an individual carries with them.

A user of the wearable device may enter into a graphical user interface a location and/or activity and sensor data that may be gathered in connection with the activity. When the location and/or activity matches what the user has entered, sensor data may be received as a measure of physiological parameters of the user.

Wearable devices, mobile devices, and geo-fence networks may communicate using any data communication technology known in the art. In certain embodiments a wearable device may communicate with a mobile device using a first type of wireless data communication technology, and the mobile device may communicate with the geo-fence network using a second type of wireless data communication technology. Data communication interfaces useful among the various embodiments include, but are not limited to cellular/3G/4G/LTE, Wi-Fi (802.11x), infrared, optical, near field, and Bluetooth data communication interfaces. In certain instances, a wearable device may include a plurality of data communication interfaces, a processor, a memory, a field programmable gate array (FPGA), an application specific integrated circuit (ASIC), etc. Mobile devices may also communicate with a wearable device over a wired data communication channel, such as a USB connection or micro USB connection.

Mobile devices described herein include, but are not limited to mobile devices such as smartphones, IPHONE devices, ANDROID devices, IPAD devices, and notebook computers. Communications communicated by a wearable device or by a mobile device may be communicated over any data communication technology known in the art, including, but not limited to Bluetooth, cellular/3G/4G/LTE, and Wi-Fi (802.11x). In certain instances, a mobile device may include a plurality of data communication interfaces, a processor, a memory, a field programmable gate array (FPGA), an application specific integrated circuit (ASIC), etc.

A geographic location or "geo-location" is a physical location that may correspond to a latitude and a longitude, a street address, attachment to a known cellular or WiFi base station, etc. In certain embodiments a geo-location may be determined using, e.g., Global Positioning System (GPS) technology in a wearable device or in a mobile device that communicates with the wearable device.

Sensor data sensed at a wearable device may be stored in memory and used by a processor to calculate, e.g., calories burned or weight lost. Raw sensor data may also be used in various embodiments, such as a number of steps counted by an acceleration sensor.

The various methods may be performed by software operating in conjunction with hardware. For example, the software may include instructions executed by a processor (e.g., a microprocessor, field programmable gate array, application specific integrated circuit, or other devices capable of processing data or otherwise performing the functions described herein), the instructions otherwise stored in a non-transitory computer readable medium such as memory (e.g., L1, L2, L3, system memory, or storage medium such as flash, magnetic, or optical media) accessible to the processor. In various embodiments, such as those utilizing ASICs to perform one or more functions described herein, the processor may be hardwired to perform such functions and, as such, the instructions described as defining such functions in various embodiments herein may be omitted in other embodiments. Various interfaces may be implemented—communications and otherwise. One skilled in the art will appreciate the various requisite components of a mobile device and integration of the same with one or more of the embodiments described herein.

FIG. 1 illustrates an example environment 100 for a wearable device 110 that is associated with monitoring a user's physiological information during various activities. FIG. 1 illustrates locations such as an individual's home 120, office 130, client 140, car 150, and other locations 160.

Figure 2:
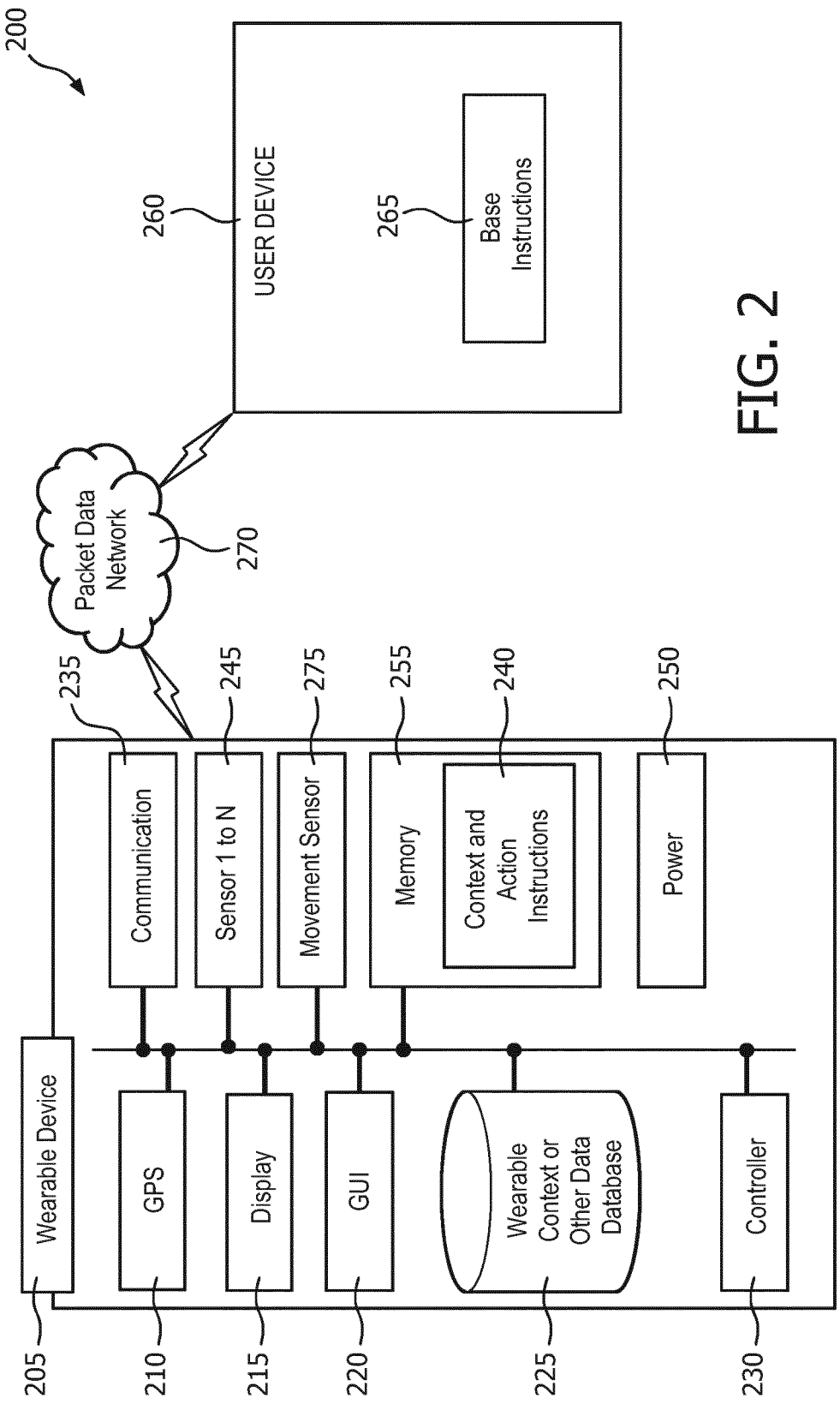
FIG. 2 illustrates an example wearable device that connects to a user device over the packet data network.

FIG. 2 illustrates an example of a wearable device 205 that connects to a user device 260 over the packet data network 270 such as, for example, a carrier network, a local area network, or the Internet. In various embodiments, at least a portion of the packet data network 270 may traverse one or more devices in a cloud computing environment. The system 200 of FIG. 2 includes a wearable device 205 that is depicted as including a global positioning system (GPS) 210, a display 215, a user interface (UI) 220, a wearable context or other database 225, a controller 230, a data communication interface 235, sensors 1 through N 245, a power supply 250, and a memory 255 which may store context and action instructions 240, as well as instructions for presenting a graphical user interface (GUI) via the display 215 and user interface 220 The user device 260 is depicted as including base instructions (software) 265 (which may be stored in a memory and executed by a processor of the user device 260). The wearable device 205 and the user device 260 are depicted as communicating over the packet data network 270. When a person wearing the wearable device 205 engages in an activity as indicated by movement data and GPS data, the context and action instructions 240 of the wearable device 205 may activate tracking of a user's physiological information gathered by sensors 1 through N 245. In some embodiments the context and action instructions 240 selectively activates sensors 245, such that the sensors 245 gather physiological data to be associated with the activity. For example, in a work meeting heart rate and skin conductance data may be gathered as a measure of stress.

As used herein, the term "processor" will be understood to include any hardware device capable of executing instructions stored in memory or otherwise processing data. As such, a processor may include a microprocessor, field programmable gate array (FPGA), application-specific integrated circuit (ASIC), or other similar devices. The term "memory" will be understood to include various memories such as, for example L1, L2, or L3 cache or system memory as well as storage memories such as flash, magnetic, optical storage media as well as other non-transitory storage media. As used herein, the term "non-transitory" will be understood to exclude transitory signals but to include all forms of storage, including both volatile and non-volatile memories. Additionally, as used herein, the term "user device" will be understood to refer to both the user devices described in connection with the user device 260 (non-wearable user devices such as mobile phones, tablets, and personal computers) as well as the wearable device 205 itself.

In some embodiments the user device 260 includes sensors 245 that track movement and GPS 210 that tracks the location of the user of the wearable device 205. In this embodiment the wearable device 205 and the user device 260 communicate over the packet data network 270.

The geo-location of the wearable device 205 may be determined by the GPS 210 at the wearable device 205 or another equivalent technology, for example, at the user device 260 (e.g., if the user device is a smart phone that includes a geo-locational device). Locations determined to be the geo-location of the wearable device 205 may include an individual's home, office, client/customer site, car, or other/unknown, as described in FIG. 1. Parameters relating to the activity and the one or more sensors 245 may be entered by the user of the wearable device 205 using a GUI 220 that may be displayed on the display 215 at the wearable device 205. In some embodiments the parameters may be pre-programmed into the wearable device 205 and the context and action instructions 240.

Figure 3:
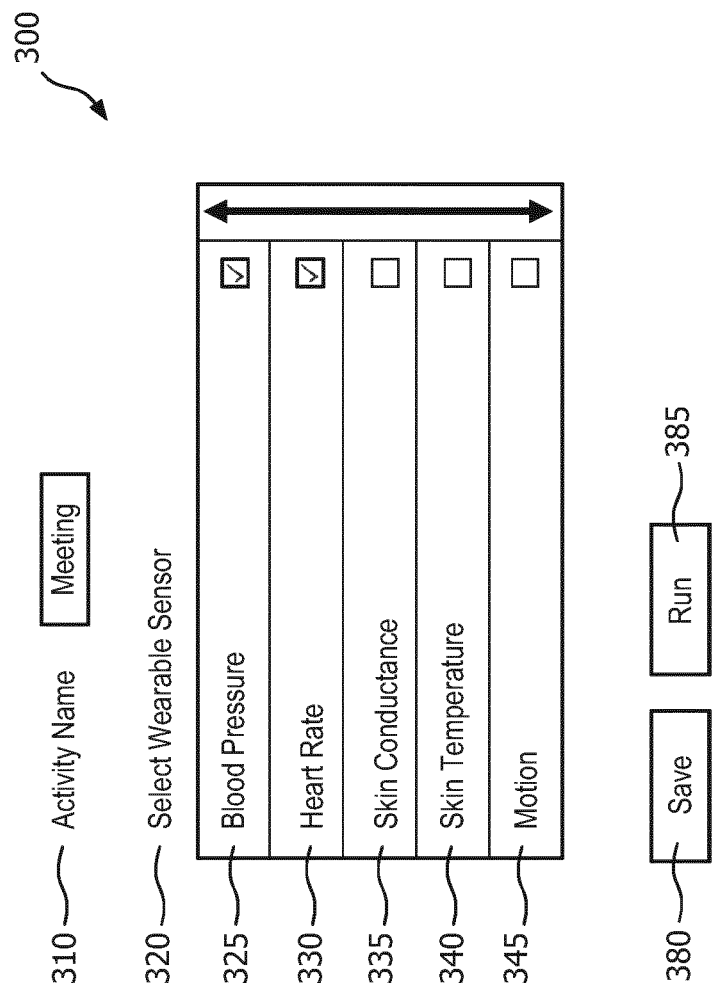
FIG. 3 illustrates an example GUI that may be displayed on a display of a wearable device.

FIG. 3 illustrates an example GUI that may be displayed on the display 215 of a wearable device 205. The GUI 300 includes a name of a location ("meeting") 310, a set of selectable sensors 320 in a wearable device 205, a save selection box 380, and a run selection box 385.

Selectable sensors 320 depicted in FIG. 3 include blood pressure 325, heart rate 330, skin conductance 335, skin temperature 340, and motion 345, though it will be understood that alternative or additional sensors (or parameters calculated therefrom) may be available for selection. Check marks in FIG. 3 depict that the blood pressure sensor 325 and the heart rate sensor 330 are enabled. The selectable sensors 320 may include values determined directly by one or more sensors (e.g., blood pressure) or values computed from sensor measurements (e.g., heart rate or calories burned). In some embodiments, It is also possible that when a particular sensor is selected from the geo-fence GUI, one or more sensors associated to with the selected sensor is automatically selected by the wearable device 205. For instance, calories used may also be determined based on the output of heart rate (HR) and motion information. Thus, in this case, though the user has selected calories used sensor 330, motion sensor(s) and heart rate sensor(s) are automatically selected.

The GUI 300 of FIG. 3 may be used by a user of the wearable device 205 to specify an activity name 310. The user may also select one or more sensors 320 that may collect physiological information about the user of the wearable device 205. In other embodiments the sensor data is automatically transferred based on a schedule item name selected by a user.

As shown in FIG. 3, collections of rules may be used advantageously to implement various programs. The rules in FIG. 3 provide a program that provides feedback to the operator of a wearable device as the operator participates in a meeting or other activity. In various embodiments additional information may be collected that is not made available to the operator, but is stored on a searchable database (either locally or remotely) for access by the operator or other users of the information.

FIG. 4 illustrates an example wearable database 400 which may correspond to the wearable database 225 of FIG. 2. A table 400 in FIG. 4 includes columns that represent fields used to determine conditions where data acquisition is to be triggered: a context name field 405 for storing a short name for identfiying each known context (e.g., a name input by the user via the activity name field 310 of the example GUI 300); a context criteria field 410 for referring to or otherwise defining criteria for determining whether each known context applies at a given time; an in context Boolean field for defining whether the wearable device and associated user are within each known context (and, therefore, that the associated sensors should be tracked or associated rules should be evaluated); a sensors field 420 for identifying any sensors or calculated parameters that should be tracked while in an associated context (e.g., as selected by the user via the example GUI 300); and a rules field 425 for referencing or otherwise defining any rules that should be considered "active" and therefore evaluated for applicability while in an associated context.

Various approaches may be taken to determine whether a user and wearable are in a context and, as such, different information may be stored in the context criteria field 410. Some contexts may be identified by comparing sensor data to a "schedule format" previously learned to correspond to the context. An example of such a schedule format will be described in greater detail below with respect to FIG. 9. Some contexts may be, instead or additionally, identified by searching other programs or device used by the user for clues as to the current (or upcoming) context. As an example, FIG. 10 will describe one embodiment that searches a calendar app on a user device for contextual clues used to identify any currently applicable contexts.

As a first example, a record 430 indicates that a user is not currently in a "Home" context, as determined by comparing recent sensor data to a schedule format identified as "schedule format A" previously learned by the device. For example, recent accelerometer, skin conductance, and temperature data may not correspond to "schedule format A"

within a tolerance of 80% and, therefore, the wearable (or other device) may have determined that the sensor data does not "match" the schedule format and the user is not currently in the "Home" context. It will be apparent that in various embodiments, various methods may be used to perform such determination of matching and that such methods may not allow for any tolerance, may allow tolerances other thant 80% similarity, or may used alternative metrics for judging "closeness" and provide tolerancein. When the "Home" context is applicable, however, no sensors or rules are defined as applicable (other than any sensors or rules that may be always applicable regardless of context, not shown).

As a second example, record 440 is seen to define a context that is the complement of the "Home" context. In particular, record 440 defines the "Not Home" context which is currently applicable and is applicable whenever recent sensor data does not sufficiently match "Schedule Format A." In some embodiments, the "Not Home" context may be user defined while, in other embodiments, the "Not Home" context may be created automatically, for example, in response to a user's creation of the "Home" context defined by record 440. As shown, when the "Not Home" context is applicable, the skin conductance sensor will be used to gather data and rules B1, B2, and B3 (which may be stored in another table, not shown) may be repeatedly evaluated for applicability. For example, rule B1 may indicate that, if heart rate (which may be a sensor that is always on or parameter that is always calculated regardless of context) raises above 120, a message should be displayed to the user indicating that they should take a seat. In various embodiments, rules may be user defined, defined by other humans (e.g., program operators) and pushed to the wearable device for activation and evaluation, or learned by a machine such as the wearable device (e.g., do not display any messages when in the meeting context).

A third example record 450 identifies a currently-occupied "Office" context that is applicable when recent sensor data matches a schedule format identified as "Schedule Format B." While in this context, the Blood Pressure and Temperature sensors are polled for data while rules A1, A2, A3, and A4 are evaluated for applicability. A final example record 460 illustrates an alternative to schedule formats for identifying occupied contexts. As shown, the "Customer Meeting" context may be identified a occupied by the user based on an indication from calendar analysis instructions that a customer meeting is underway (e.g., through the calendar analysis instructions returning the "Customer Meeting" keyphrase). As will be explained in greater detail below, various embodiments of calendar (or other app) analysis instructions may evaluated the titles, user-supplied tags, or other information associated with calendar entries (or other app items) to determined a current context to be reported for use in conjunction with the database 400. The database may include numerous additional entries 460.

Figure 5:
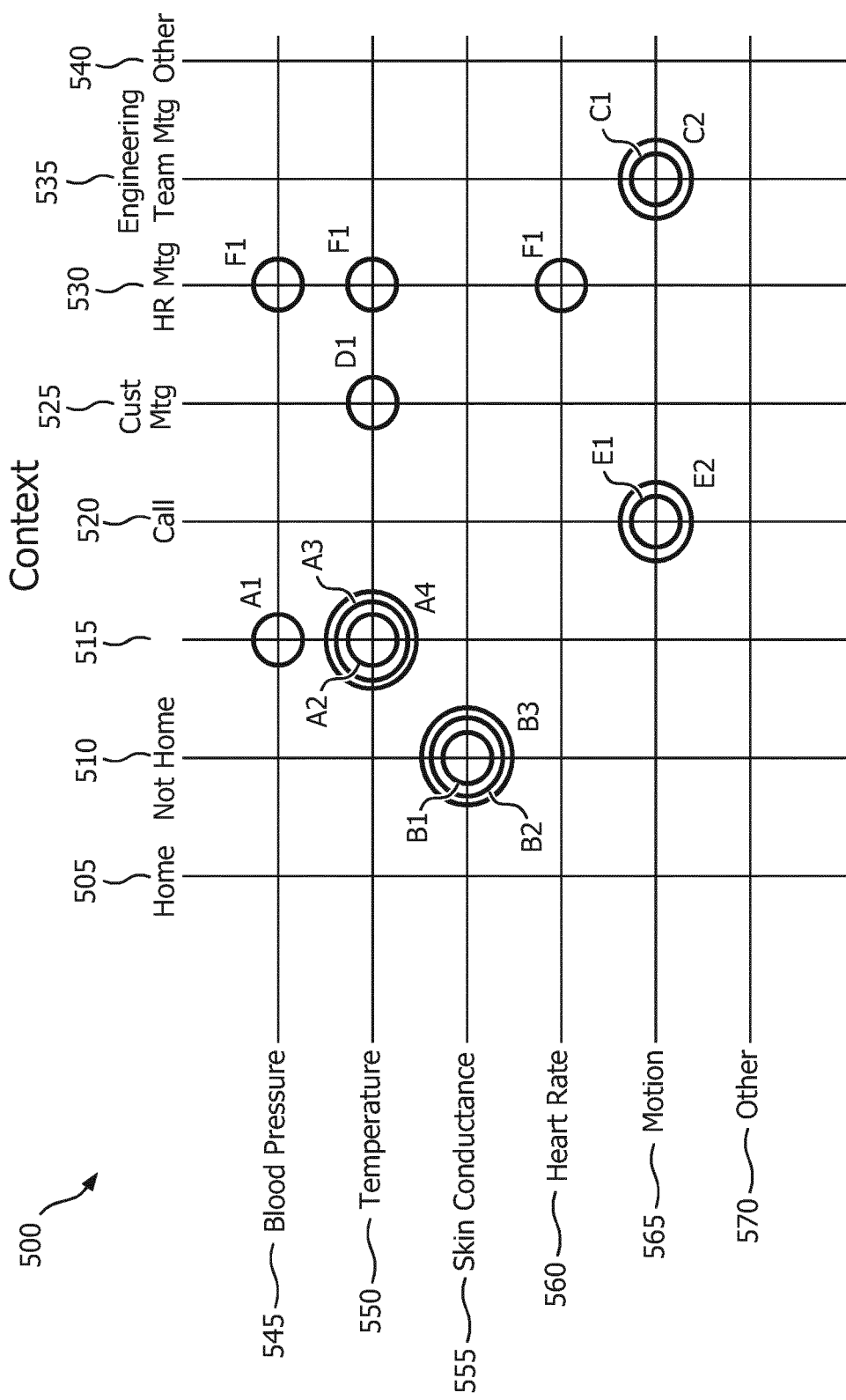
FIG. 5 illustrates an example association among wearable sensor data and locations.

FIG. 5 illustrates an example diagram 500 illustrating the cross-referencing of different kinds of schedule items with different contexts and data sensed by a sensor at a wearable device. The sensor and context cross-reference diagram 500 of FIG. 5 includes places of: at home 505, not home 510, office 515, call 520, a customer meeting 525, HR meeting 530, an engineering meeting 535, and another place 540. Information that corresponds to data sensed by or derived from a sensor at the wearable device include: blood pressure 545, temperature 550, skin conductance 555, heart rate 560, motion 565, and other 570.

The circles in FIG. 5 identify example instances where one or more rules apply in a specified location to specified sensor information sensed by a wearable device. FIG. 5 indicates that location office 515 that blood pressure sensor 545 will be triggered using rule A1. Similarly, location not home 510 and skin conductance 555 will be triggered by rules B1, B2, and B3; location office 515 and temperature sensor 550 will be triggered by rules A2, A3, and A4; location call 520 and motion sensor 565 will be triggered by rules E1 and E2; client/customer meeting 525 and temperature sensor 550 will be triggered by rule D1; location HR meeting 530 and heart rate sensor 560 will be triggered by rule F1, and engineering meeting 535 and motion sensor 565 will be triggered by rules C1 and C2. Other relationships between the locations, rules, sensors and may exist and may be programmed according to the needs of the operator or an administrator, in particular, which physiological parameters are desired to be tracked.

Figure 6:
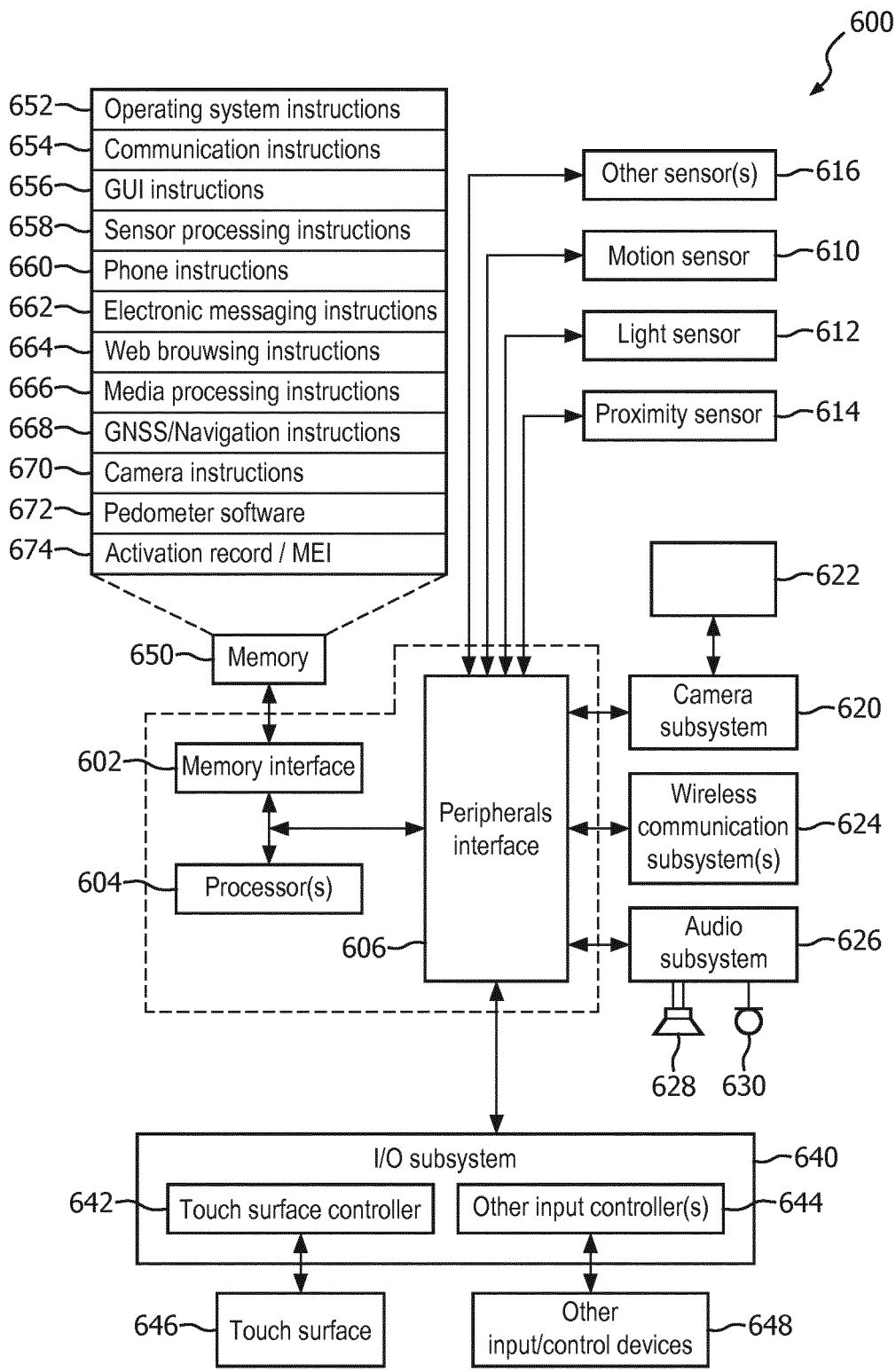
FIG. 6 illustrates a mobile device architecture that may be utilized to implement the various features and processes described herein.

FIG. 6 illustrates a mobile device architecture that may be utilized to implement the various features and processes described herein. Architecture 600 can be implemented in any number of portable devices including but not limited to smart wearable devices. Architecture 600 as illustrated in FIG. 6 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 6 are meant to be inclusive of data processors, image processors, central processing units, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be implemented as an accelerometer or gyroscope, may be utilized to detect movement and orientation of the mobile device. Display objects or media may then be presented according to a detected orientation (e.g., portrait or landscape).

Other sensors may be coupled to peripherals interface 606, such as a temperature sensor, a biometric sensor, vitals sensor, or other sensing device to facilitate corresponding functionalities. Location processor 616 (e.g., a global positioning system) may be coupled to peripherals interface 606 to allow for receipt of geo-location data thereby facilitating geo-positioning. An electronic magnetometer 616 such as an integrated circuit chip may in turn be connected to peripherals interface 606 to provide data related to the direction of true magnetic North whereby the mobile device may enjoy compass or directional functionality. Camera subsystem 620 and an optical sensor 622 such as a charged coupled device (CCD) or a complementary metal-oxide semiconductor (CMOS) optical sensor may facilitate camera functions such as recording photographs and video clips.

Communication functionality may be facilitated through one or more communication subsystems 624, which may include one or more wireless communication subsystems. Wireless communication subsystems 624 may include 802.5 or Bluetooth transceivers as well as optical transceivers such as infrared. Wired communication system may include a port device such as a Universal Serial Bus (USB) port or some other wired port connection that may be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.5 communication networks, code division multiple access (CDMA) networks, or Bluetooth networks. Communication subsystem 624 may include hosting protocols such that the device may be configured as a base station for other wireless devices. Communication subsystems may also allow the device to synchronize with a host device using one or more protocols such as TCP/IP, HTTP, or UDP.

Audio subsystem 626 may be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 may be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 may display virtual or soft buttons and a virtual keyboard, which may be used as an input/output device by the user.

Other input controllers 644 may be coupled to other input/control devices 648 such as one or more buttons, rocker switches, thumb-wheels, infrared ports, USB ports, and/or a pointer device such as a stylus. The one or more buttons (not shown) may include an up/down button for volume control of speaker 628 and/or microphone 630. In some implementations, device 600 may include the functionality of an audio and/or video playback or recording device and may include a pin connector for tethering to other devices.

Memory interface 602 may be coupled to memory 650. Memory 650 may include high-speed random access memory or non-volatile memory such as magnetic disk storage devices, optical storage devices, or flash memory. Memory 650 may store operating system 652, such as Darwin, RTXC, LINUX, UNIX, OS X, ANDROID, WINDOWS, or an embedded operating system such as VXWorks. Operating system 652 may include instructions for handling basic system services and for performing hardware dependent tasks. In some implementations, operating system 652 may include a kernel.

Memory 650 may also store communication instructions 654 to facilitate communicating with other mobile computing devices or servers. Communication instructions 654 may also be used to select an operational mode or communication medium for use by the device based on a geographic location, which may be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; pedometer instructions 672 for tracking the number of steps taken by the holder of a portable device or a smart wearable device; activation record/IMEI data 674 to permit a portable device or a smart wearable device to exchange data over wireless networks; and instructions for any other application that may be operating on or in conjunction with the mobile computing device. Memory 650 may also store other software instructions for facilitating other processes, features and applications, such as applications related to navigation, social networking, location-based services or map displays.

Figure 7:
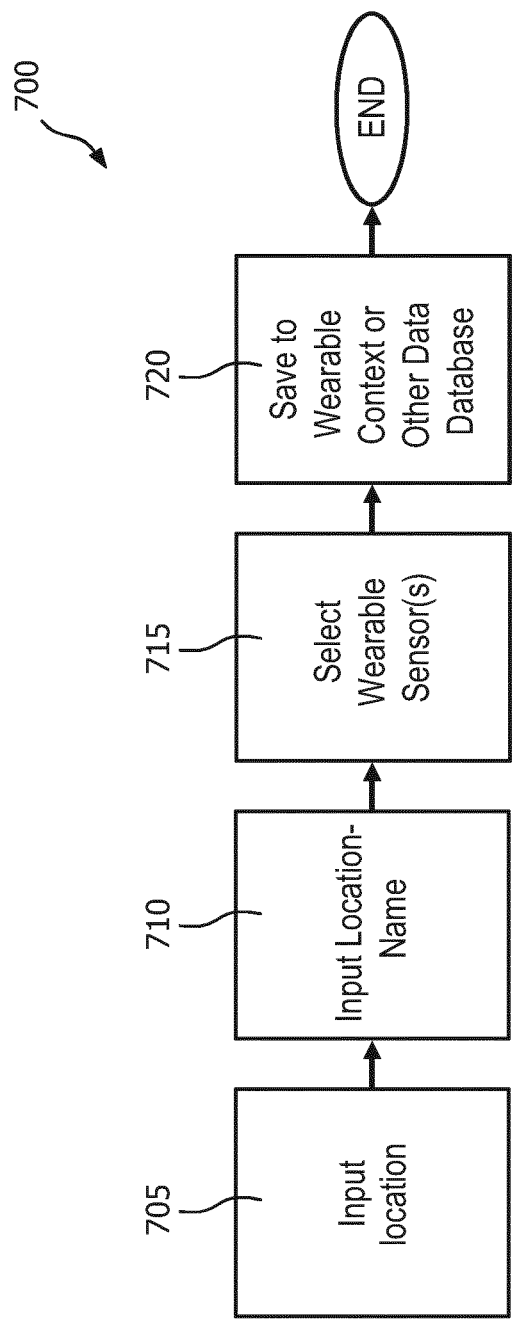
FIG. 7 illustrates an example methodology that may be executed by a context instructions.

FIG. 7 illustrates an example methodology 700 that may be executed by a context and action instructions 240. The methodology illustrated in FIG. 7 corresponds to the definition of a conditional action using a GUI 220 and includes the steps of receiving an input of a location 705, receiving an input identifying a name for the location 710 using the GUI, and receiving a selection of at least one sensor in the GUI 715. After this information is received it may be saved in a database 720 at the wearable device or in an external context or other database. The external context or other database may be located, e.g., at a computer network accessible over the packet data network.

Figure 8:
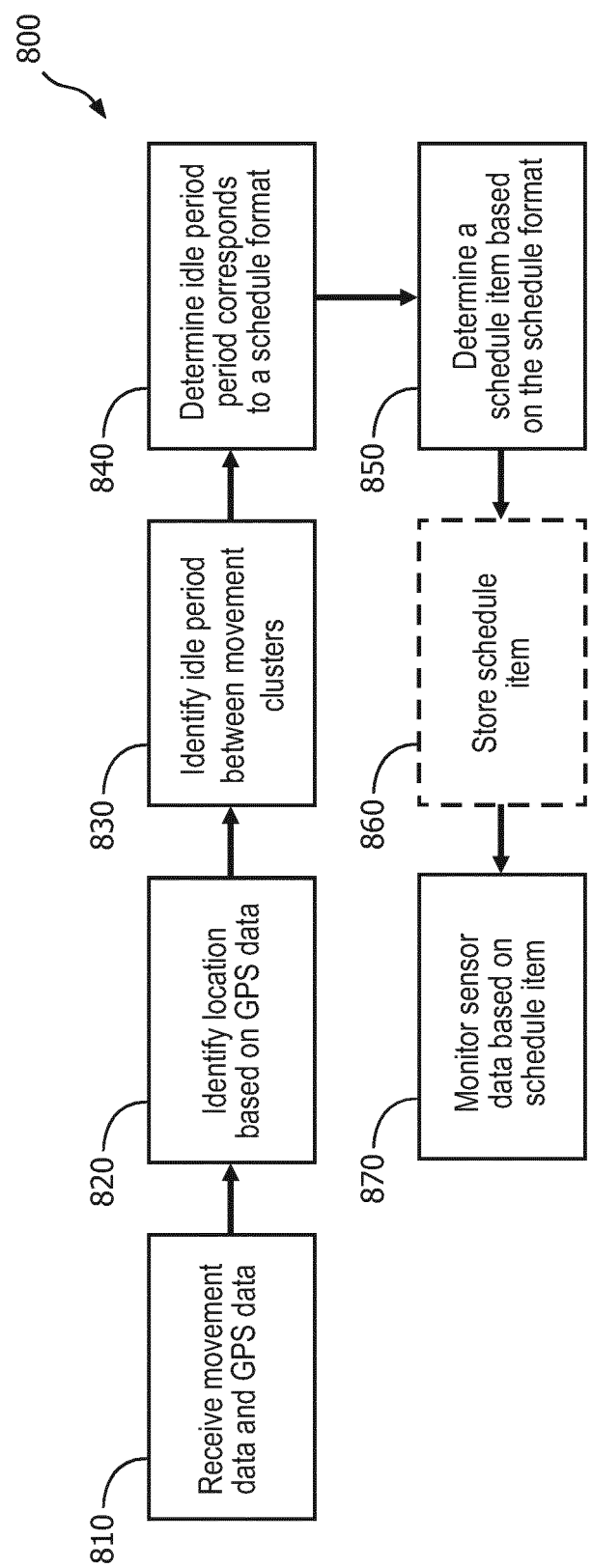
FIG. 8 illustrates example action instructions that may be executed by a processor at a wearable device.

FIG. 8 illustrates example method 800 for implementing context and action instructions 240 that may be executed by a processor at a wearable device 205. The method of FIG. 8 includes a first step 810 that receives movement data and GPS data. The movement data and GPS data may come from sensors and geo-locational devices in the wearable device 205 or the user device 260. Next in step 820 of the method, the location of the wearable device 205 is determined based on the GPS data. For example, the location may be "home," "office," or a client site. The instructions may also determine that the location is not a known location, such as "not at home," "not at the office," or "other." Next on step 830, the context and action instructions 240 identifies an idle period between two movement clusters based on the movement data. In Step 840, based on movement cluster and idle period, the context and action instructions 240 identifies the movement cluster and idle period corresponding to a format of a schedule item. In some embodiments, the correspondence need not be perfect, and may simply correlate by a threshold (e.g., 90%). For example, if the movement clusters correspond to the beginning and end of an hour (e.g., 9 a.m. and 10 a.m.) that would correspond to a meeting. In Step 850, based on the determination that the movement clusters correspond to a schedule format, the instructions identify a schedule item for the movement clusters based on the schedule format. The context and action instructions, in step 860, stores the schedule item. In step 870, the context and action instructions monitor the sensor data correlated to the schedule item based on the rules illustrated in FIG. 5. Monitoring the sensor data may include querying one or more sensors for data or querying a database of sensor data based on the date and time associated with the schedule item.

In some embodiments the movement data and GPS data may not correspond to a known schedule item. In another embodiment, the context and action instructions 240 may, via the display 215 and GUI 220, prompt an operator to either confirm or enter a schedule item.

Figure 9:
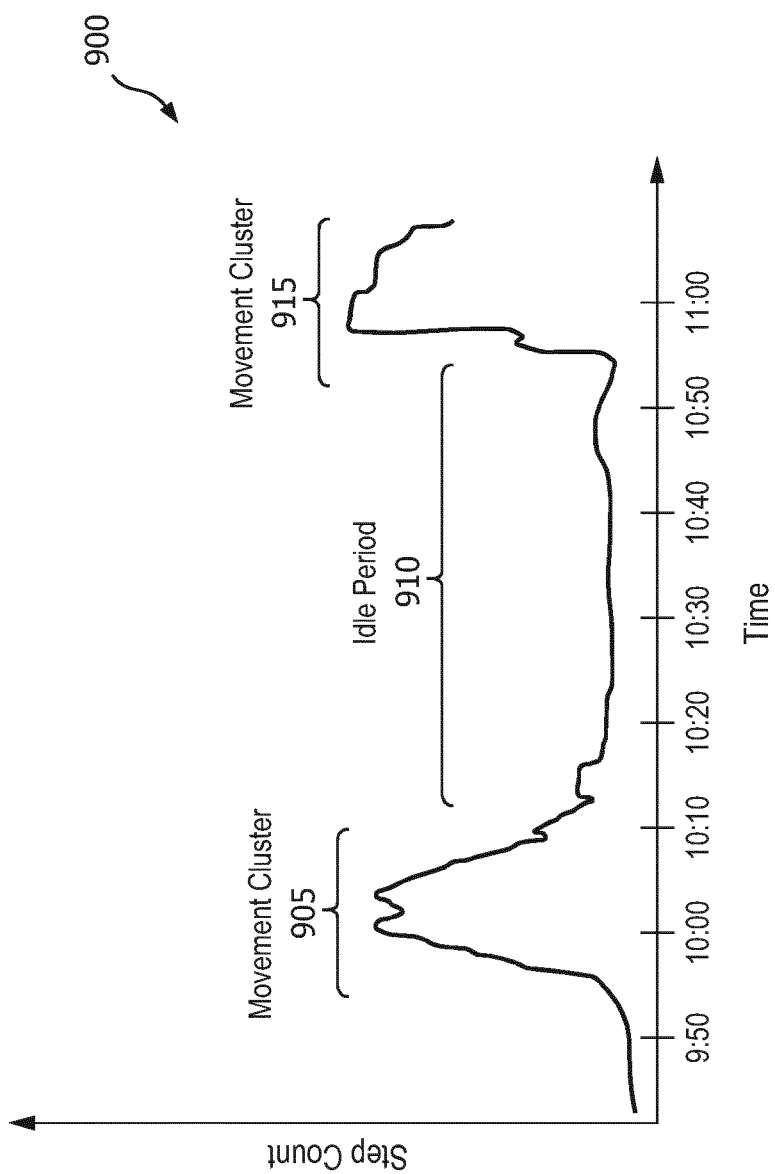
FIG. 9 illustrates a graph of an example set of movement data that corresponds to a meeting schedule format.

FIG. 9 illustrates an example schedule format 900 for a meeting. As shown, there are two movement clusters 905 and 915 separated by an idle period 910 where reduced step activity is detected, as compared to the movement clusters 905, 915. Movement cluster 905 may correspond to the beginning of the hour, 10:00 am, while movement cluster 915 corresponds to the end of the hour, 11 am.

As noted above, in various embodiments, the schedule format 900 may be compared against recently-received sensor data to determine whether the user is in an associated context. In various embodiments, the schedule format 900 may be manually-defined or may be constructed by a computer such as the wearable device, for example, utilizing machine learning principles. Accordingly, it will be apparent that, while the schedule format 900 is illustrated as a two dimensional graph, that various alternative implementations may be used (e.g., parameters of a classification model) and that additional dimensions (e.g., additional or alternative sensor measurements or calculated parameters) may be used in the schedule format.

In embodiments where the wearable device or other computer learns the schedule format for a context, the schedule format may be preset to a default format (e.g., after manual context creation via the example GUI 300). For example, all new contexts may begin with a schedule format indicating zero steps at all times of day and associated with a 0% or otherwise low confidence rating, to prevent frequent false-positives in the early operation of the device. Alternatively, in some embodiments, various contexts may be preprogrammed into the device and associated with non-user-specific models that may be further adapted to the user through learning. Alternatively, upon the user manually creating a context, the name may be compared to various preprogrammed context names and thereby associated initially with such a context specific schedule format instead of the generic schedule format. For example, if the user manually creates a "meeting" or "customer meeting" schedule format, the wearable device may determine, based on the name, that the default schedule format associated with a "meeting" should be used instead of the generic, all zeroes schedule format.

During operation, the user may proved feedback to assist the learning algorithm to the user's specific habits in various ways. For example, the user may periodically explicitly indicate which contexts they are currently within via a GUI, not shown. Similarly, the wearable may periodically ask the user to make such an identification. As the wearable begins to make determinations as to the current context, it may ask the user for confirmation that the correct decision was made (e.g., "are you currently in a meeting?" or "were you in a meeting from 10 am to 11 am?"). Alternatively, the user may be provided with a GUI to "turn off" various contexts that may have been erroneously identified by the wearable. All such feedback may be associated with the sensor data that was available at the time of each decision or feedback point, thereby progressively creating a labeled training set from which the wearable or other supporting device may adapt the schedule format.

In the particular example shown, the wearable may determine that, when a movement cluster 905 transitions to an idle period 910 at the top of the hour (10:00 as shown), that the user is currently in a "Meeting" context. Thus, in various embodiments, a schedule format specifies various characteristics of a context such as periods of high and low activity (e.g., as measured by a pedometer or accelerometer), heart rate, stress, or other sensed or computed physiological parameters; periods where a physiological parameter is within a specified range; periods where a state has been detected by the sensors (e.g., onset of sleep); transitions between states, physiological parameter values or ranges; transition of a physiological parameter across a threshold; etc. Such characteristics may be specified in isolation or may be specified in various combinations, permutations, or other relationships with respect of each other. For example, in some embodiments, a schedule format may define a transition from one period to another at an identified time (or date). The identified time may be defined as a literal time (e.g., 10:00 am); may be a class of times such as "top of the hour" (e.g., 9:00, 10:00, 11:00, etc.), "at a half hour" (e.g., 9:00, 9:30, 10:00, etc.); or may be relative to another period (e.g. "after at least 1 hour of the previous period").

Figure 10:
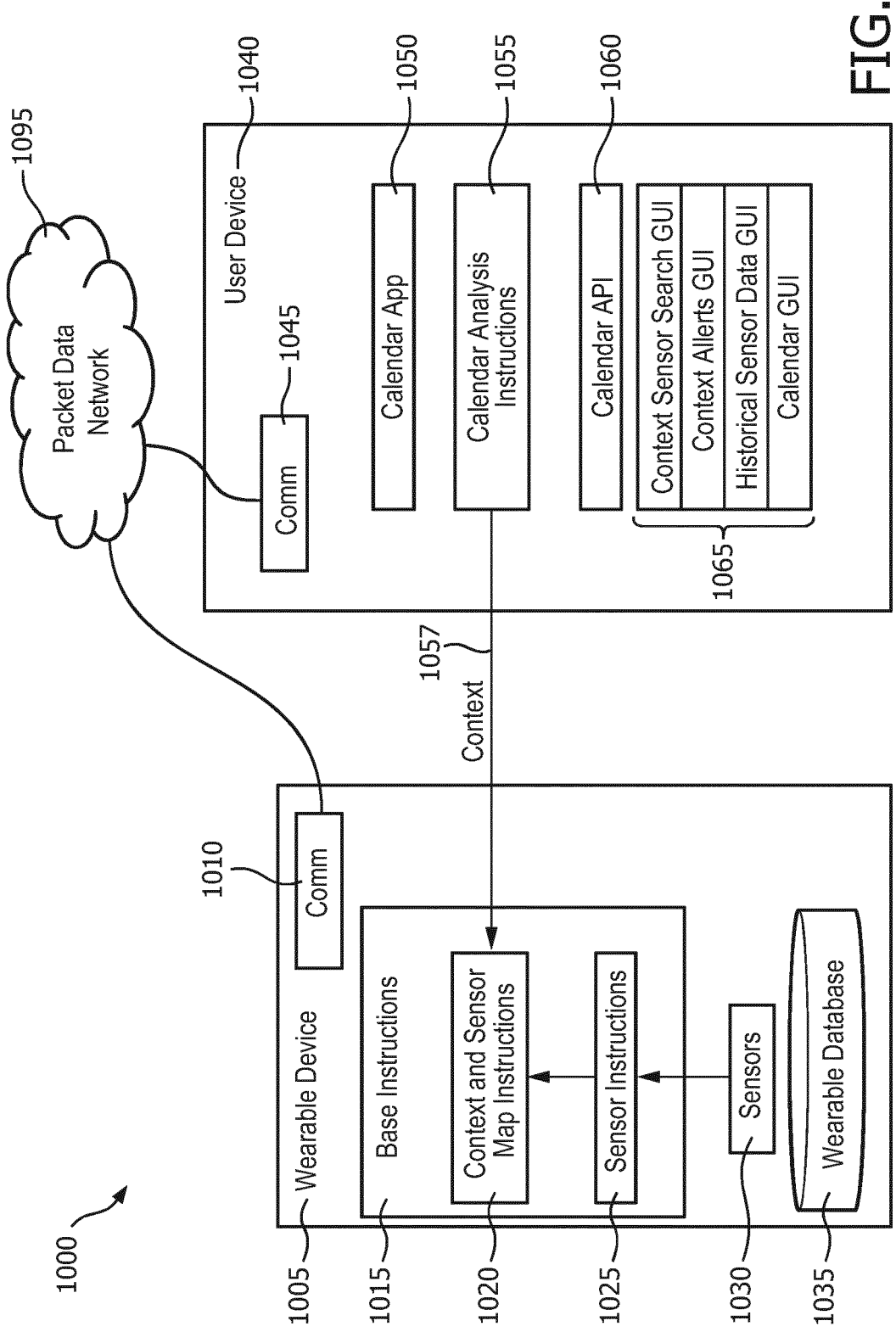
FIG. 10 illustrates example system architecture for some embodiments.

FIG. 10 illustrates an example architecture for the system of various embodiments that use additional context information to identify schedule items. The system 1000 may include a wearable device 1005 and a user device 1040. Each of the components of the system may be connected to the packet data network 1095 used to communicate with other components in the system.

The wearable device 1005 may include a communications module 1010. The communication module 1010 provides a connection to the user device 1040. The connection may be wired (e.g., USB connector) or wireless (e.g., Bluetooth). The communication module may also connect with the packet data network 1095 using Wi-Fi or cellular data connections.

The wearable device 1005 may also include base instructions 1015, which will be understood (along with other software, instructions, or applications described herein) to be stored in a memory device (not shown) and executed by a processor (not shown). The base instructions 1015 manage major functions of the wearable device 1005.

Included in the base instructions 1015 may be a context and sensor map instructions 1020 and sensor instructions 1025. The context and sensor map instructions 1020 acquires context data 1055A from the user device 1040 and then maps the sensors based on the context data received 1057. The sensor instructions controls 1025 the sensors 1030 of the wearable device 1005 to extract sensor data for measurement. In some embodiments the calendar data is processed by an analysis tool remote from the user device 1040 and then the results are provided to the context and sensor map instructions 1020.

The wearable device 1005 also includes a wearable database 1035, which may be stored in a storage or other memory device (not shown). The wearable database 1035 stores sensor data and context data 1057 from applications sent from the user device 1040.

As shown in FIG. 10, the user device 1040 may include a communication module 1045. The communication module 1045 may be used to connect the user device 1040 to the wearable device communication module 1010. The connection may be performed using the packet data network, Wi-Fi connection, hard-wired connection (e.g., Ethernet), or other data connection known in the art.

The user device 1040 may also include one or more applications containing context terms to be extracted. Example applications may include a calendar application 1050 although there may be many different applications in which the methods, systems, and principles described herein are applicable such as, for example, email, messaging, and internet browser applications (not shown).

The user device 1040 may also include an application analysis instructions (e.g., calendar analysis instructions) 1055. The analysis instructions 1055 may be used to analyze the application data and use context to determine the context of any one entry in the application (e.g., one calendar event).

The user device 1040 may also include an application programming interface (API) for the application. For example, as shown in FIG. 10, the user device has a calendar API 1060. The API allows other instructions to communicate with the application found in the user device. Furthermore, the API allows other instructions to extract data from the user device and/or supply data to the user device.

The user device 1040 may also include a set of graphic user interface (GUIs) 1065 (which may be embodied as sets of instructions for execution by a processor to present and receive information via various user interface components such as a display, touchscreen, buttons, speaker, etc.). The set of GUIs 1065 may include a context sensor search GUI, a context alerts GUI, a historical sensor data GUI, a calendar GUI, etc. Examples of these GUIs may be seen, for example, in FIGS. 16 and 17.

The system described in FIG. 10 may facilitate the use of context information that is found within a calendar to enhance the context information, detecting meeting items in a user's schedule. For example, from the GPS and movement analysis the context and action instructions may determine that a meeting occurred at the office on a certain date. By analyzing the user's calendar, additional information may be determined, such as that the meeting was with a supervisor, or that the meeting was with an engineering team working on a time sensitive project. This facilitates learning by an organization about its personnel. For example, the sensors carried by personnel working on a time sensitive project may measure physiological parameters that indicate a high level of stress when they meet to discuss a project.

Figure 11:
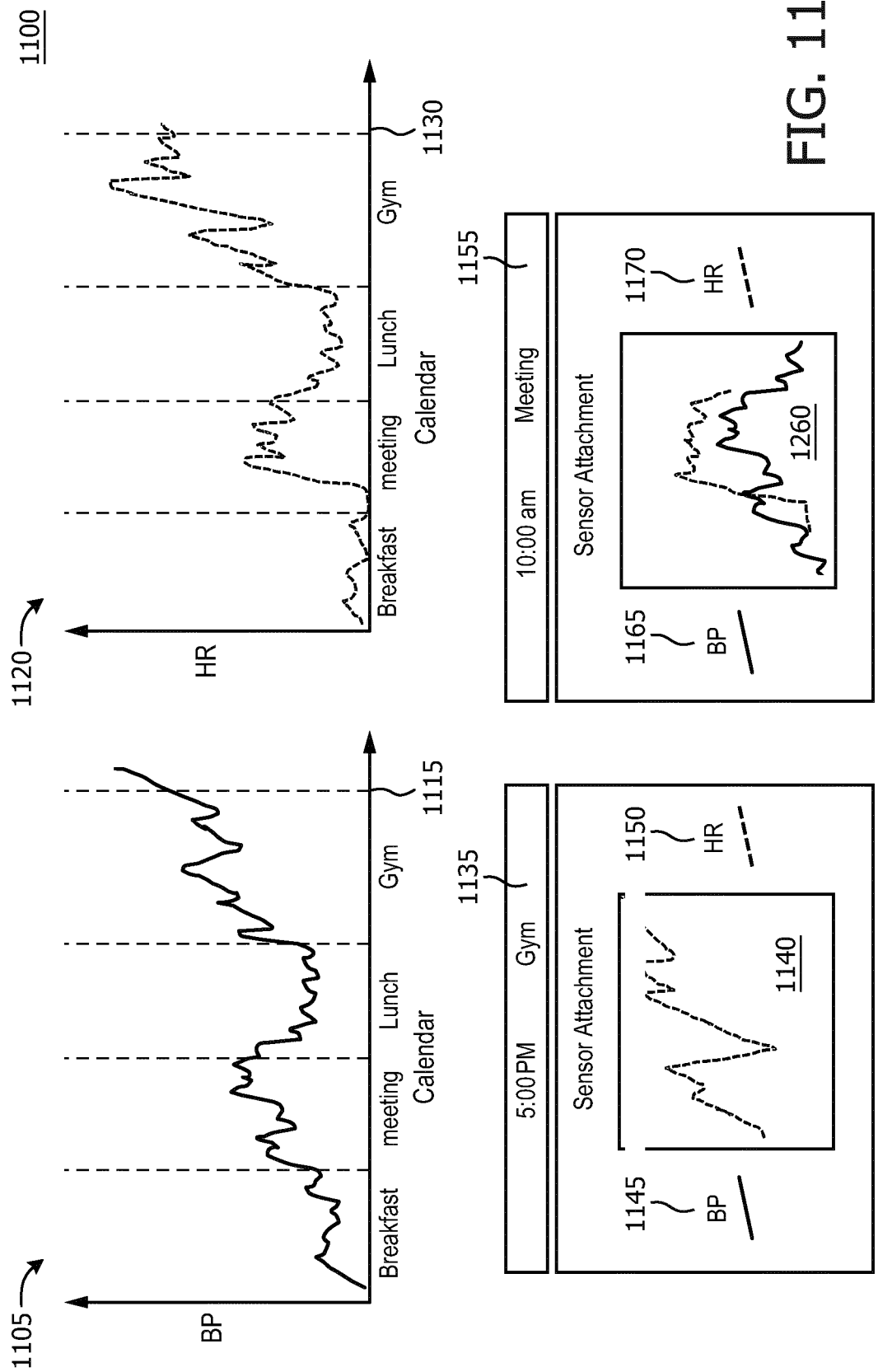
FIG. 11 illustrates example sensor data associated with corresponding calendar appointments.

FIG. 11 illustrates example sensor data 1100 with corresponding calendar appointments. A top portion of FIG. 11 shows example graphs of data for blood pressure 1105 and heart rate 1120 for a user versus time. The graphs subdivide time along a horizontal axis 1115 and 1130 organizing the time by calendar appointments (e.g., meals, meetings, gym). The blood pressure graph 1105 includes a vertical axis that may display a measure of blood pressure. The heart rate graph 1120 includes a vertical axis that may display a measure of heart rate.

By organizing the sensor data using the subdivisions the user may be provided with the data and one or more related contexts for the data in a graph. For example, the heart rate graph 1120 presents the measured heart rate organized against events on the calendar axis 1130. Notice that the heart rate varies throughout the day. At breakfast and at lunch the user heart rate is low, when attending a meeting the user heart rate is moderate, and when at the gym the user heart rate is high.

The bottom portion of FIG. 11 shows a first graph 1140 including data for blood pressure 1145 and heart rate 1150 that is associated with a gym appointment 1135. The bottom portion of FIG. 11 also includes a second graph 1160 that shows data for blood pressure 1165 and heart rate 1170 that is associated with a meeting 1155.

In general, FIG. 11 shows examples of wearable data that may be associated with calendar appointments. In particular, the wearable data and the calendar appointments 1135 and 1155 may further be viewed by the user in relation to each other in terms of time or by appointments.

Figure 12:
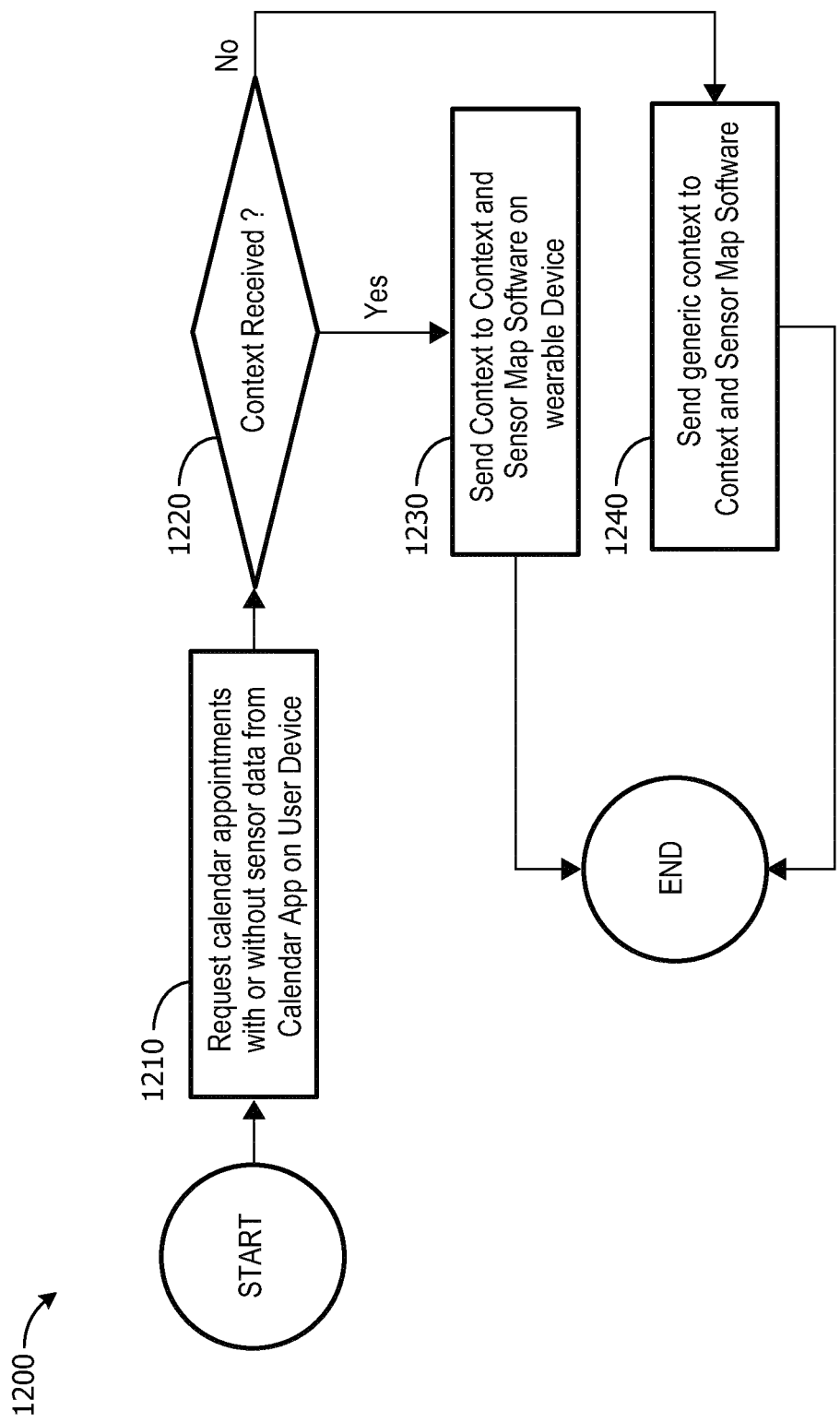
FIG. 12 illustrates example calendar analysis instructions.

FIG. 12 illustrates an example method 1200 for implementing the calendar analysis instructions 1055 of FIG. 10. In particular, the application analysis instructions 1200 are applied to a calendar application.

At the start of the application analysis instructions, the application analysis instructions may request calendar appointments with or without accompanying sensor data from the calendar application in step 1210.

Context data may be retrieved from local or network storage 1220. The software is terminated after some context data is provided to the context and sensor map instructions 1230, 1240. For example, when the context data is received in step 1220, the method 1200 proceeds to step 1230, where the calendar analysis instructions passes the context received in step 1220 back to the context and sensor map instructions on the wearable device. On the other hand, if the requested context is not received in step 1220, the method 1200 proceeds to step 1240 where the calendar analysis instructions returns a generic context to the context and sensor map instructions on the wearable device. After a context is returned, the method 1200 proceeds to end.

Figure 13:
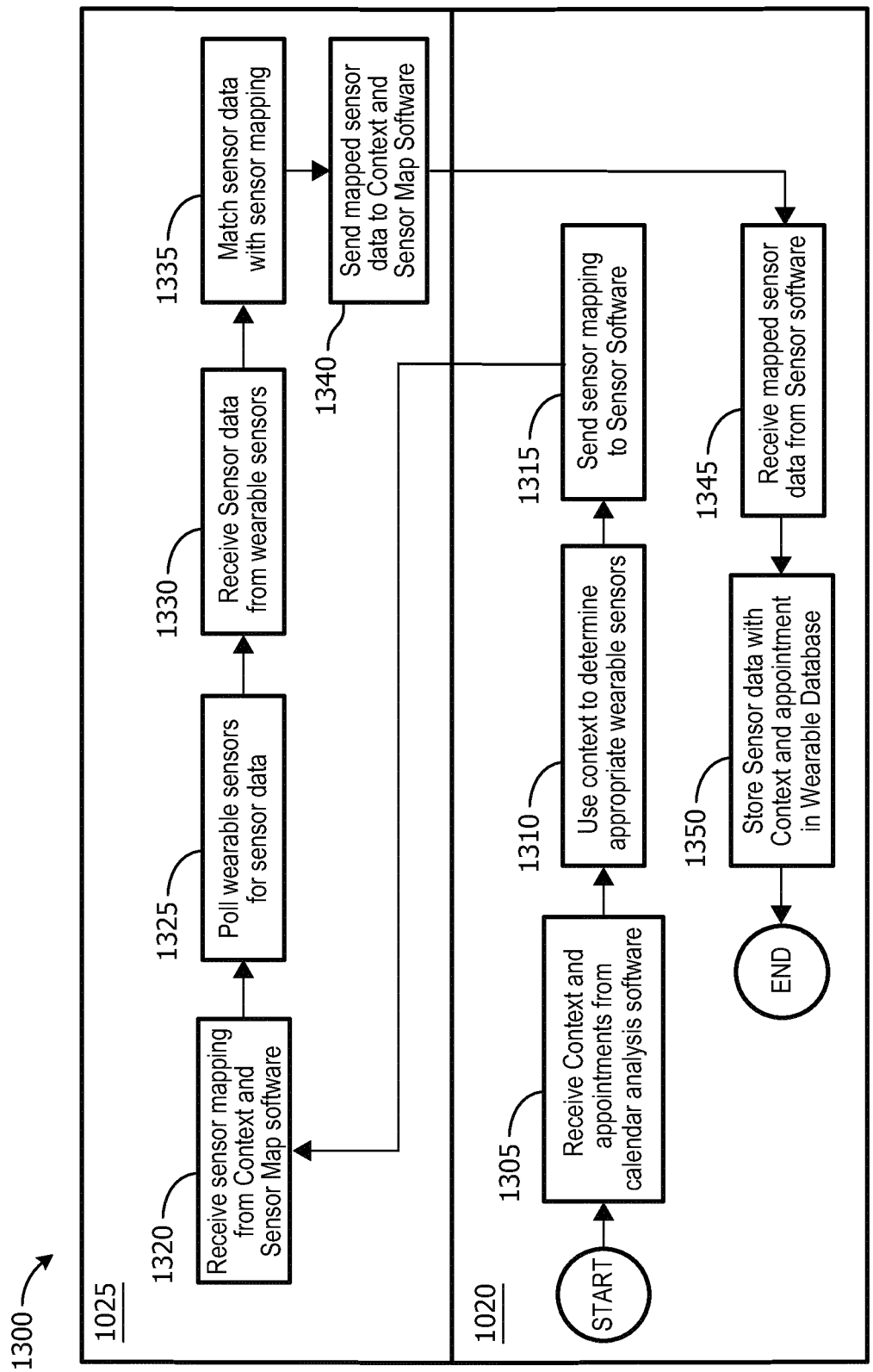
FIG. 13 illustrates example context and sensor map instructions.

FIG. 13 illustrates an example method 1300 for implementing the sensor instructions 1025 and context and sensor map instructions 1020 of FIG. 13.

The overall method 1300 for the sensor instructions 1025 and the context and sensor map instructions 1020, shown in FIG. 13, starts at the context and sensor map instructions. The context and sensor map instructions 1020 may first receive context data and appointments from 1305 the application (e.g., calendar) analysis instructions on the user device 1040. This information is matched to the schedule items identified using the movement data and GPS data. The appropriate wearable sensors 1030 are determined next using the context data 1310 and the schedule item. For example, if the schedule item corresponds to a meeting, and the context data is related to a meeting with HR, the method may only select data collected from the blood pressure, skin temperature, and heart rate sensors, which may both be indicators of stress levels. Once a context is determined in step 1305 and the sensors are determined in step 1310, a mapping of the sensors may be sent to sensor instructions in step 1315.

After the sensors have been selected based on the context data, the sensor instructions 1025 will start. The sensor instructions 1025 will receive the selection of the sensors 1320 from the context and sensor map instructions 1020. The sensor instructions 1025 will then poll wearable sensors for sensor data 1325. The sensor instructions 1025 may then receive sensor data from the sensors on the wearable device in step 1330.

The sensor instructions 1025 may then match the sensor data with the data from the context and sensor map instructions 1020 in step 1335. Finally, the matched data may then be sent back to the context and sensor map instructions 1020 in step 1340 where the instructions will receive mapped sensor data in step 1345 and store the matched data in the database of the wearable device in step 1350.

As a quick overview, the context and sensor map instructions 1020 receives context data from the user device 1305. The context data is defined using the wearable context network. The context and sensor map instructions 1020 will then use the context data to determine which sensors should be used 1310.

The sensor map data may be sent to the sensor instructions 1315. The sensor instructions may retrieve sensor data from the physical sensors of the wearable device 1320. The sensor instructions may allocate sensor data based on the mapping sent 1315 from the context and sensor map instructions. The sensor instructions then returns the mapped data 1340 to the context and sensor map instructions. The context and sensor map instructions then stores 1350 the mapped data, for example, as a record in a database correlating the sensor data, timestamp, or determined context. The mapped data may be used by the user device and several other applications based upon its context and associated calendar appointment. For example, the use device, wearable device, or a cloud-based device administering a coaching program may determine that, when a particular recurrent meeting is associated with high stress levels, that messages (e.g., content cards providing coaching insights) should be delayed to a later, less stressful time.

This method is advantageous in that it allows context associated with one or more keywords in an appointment to determine the sensors to be used in connection with the execution of conditional actions, without requiring a user to manually configure the sensors used.

FIG. 14 illustrates an example wearable database 1400. As shown in FIG. 14, information for the wearable database is shown as a grid with columns and rows in a table 1400. The columns may represent data fields including context 1405 and name 1410. Other columns included in the table 1400 are sensor 1 1415 and corresponding sensor 1 data 1420, sensor 2 1425 and corresponding sensor 2 data 1430, and sensor N 1435 and corresponding sensor N data 1440.

As shown in FIG. 14, an example context data entry that may be found in the wearable database 1135 may be as depicted in row 1445. The name of the meet at the office may be "meeting with boss," as illustrated where column 1410 crosses with row 1445. The first sensor associated with this appointment may be blood pressure, as illustrated where column 1415 crosses with row 1445. And the sensor data may be displayed in a graphical format, as illustrated where column 1420 crosses with row 1445. An entry in the table may also correspond to an average of blood pressure over the time span of the meeting (not illustrated). A second sensor may be a heart rate monitor that provides sensor data associated with the heart rate, as illustrated where column 1425 crosses with row 1445. Another sensor, sensor N may be a temperature sensor. The temperature sensor data may include sensor data that is associated with an exercise performed by a user of the wearable device, as illustrated where column 1435 crosses with row 1450.

Another example context data entry is illustrated in row 1455, named "Anniversary Dinner." This event is classified as a "Personal" event, in contrast to the other events classified as "Work" and "Exercise." The first sensor associated with this appointment may be blood pressure, as illustrated where column 1415 crosses with row 1455. And the sensor data may be displayed in a graphical format, as illustrated where column 1420 crosses with row 1455. An entry in the table may also correspond to an average of blood pressure over the time span of the meeting (not illustrated). A second sensor may be a heart rate monitor that provides sensor data associated with the heart rate, as illustrated where column 1425 crosses with row 1455. Another sensor, sensor N may be a temperature sensor, as illustrated where column 1435 crosses with row 1455.

It should be noted that the entries in FIG. 14 for the wearable database are example and illustrative. The wearable database can include many more and different types of entries. Additional information may also be included in the wearable database aside from what is shown in FIG. 14.

Certain features may be implemented in a computer system that includes a back-end component, such as a data server, that includes a middleware component, such as an application server or an Internet server, or that includes a front-end component, such as a client computer having a graphical user interface or an Internet browser, or any combination of the foregoing. The components of the system can be connected by any form or medium of digital data communication such as a communication network. Some examples of communication networks include LAN, WAN and the computers and networks forming the Internet. The computer system can include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an API that can define on or more parameters that are passed between a calling application and other software code such as an operating system, library routine, function that provides a service, that provides data, or that performs an operation or a computation. The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API. In some implementations, an API call can report to an application the capabilities of a device running the application, such as input capability, output capability, processing capability, power capability, and communications capability.

Figure 15:
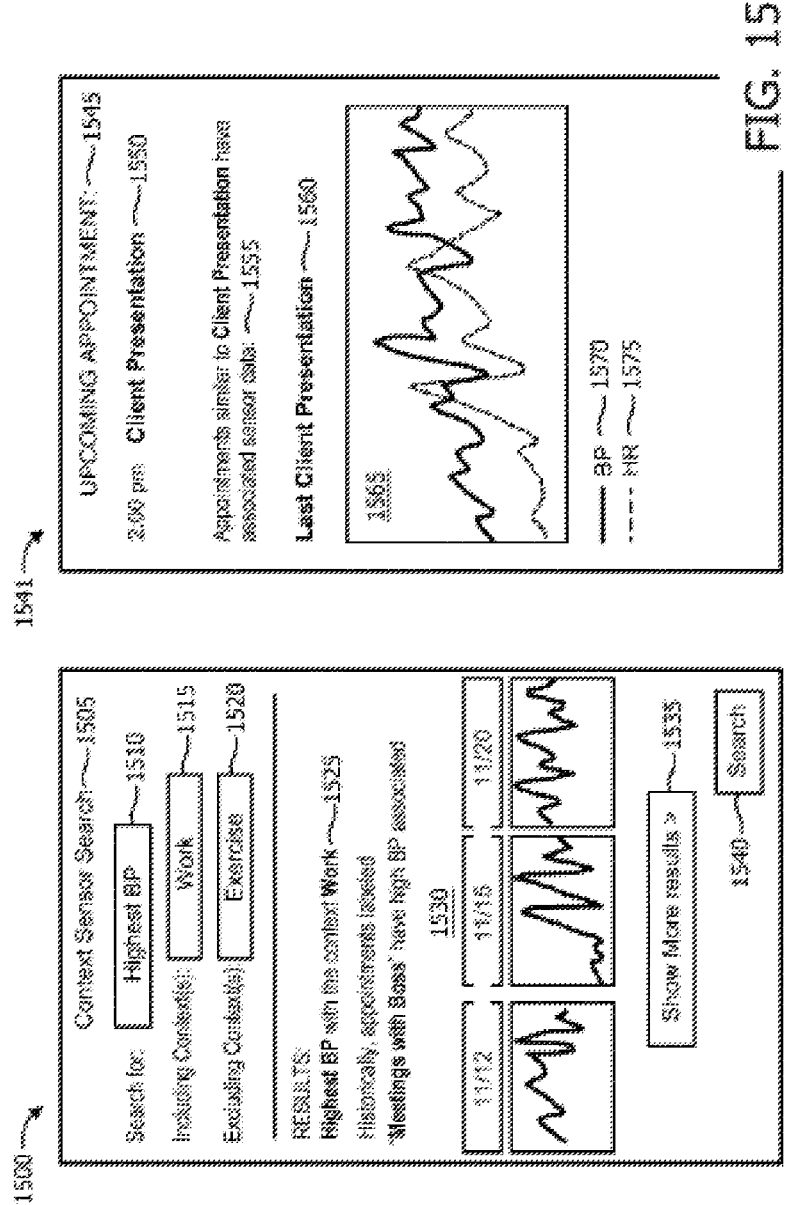
FIGS. 15-16 illustrate example graphical user interfaces in accordance with various embodiments.
Figure 16:
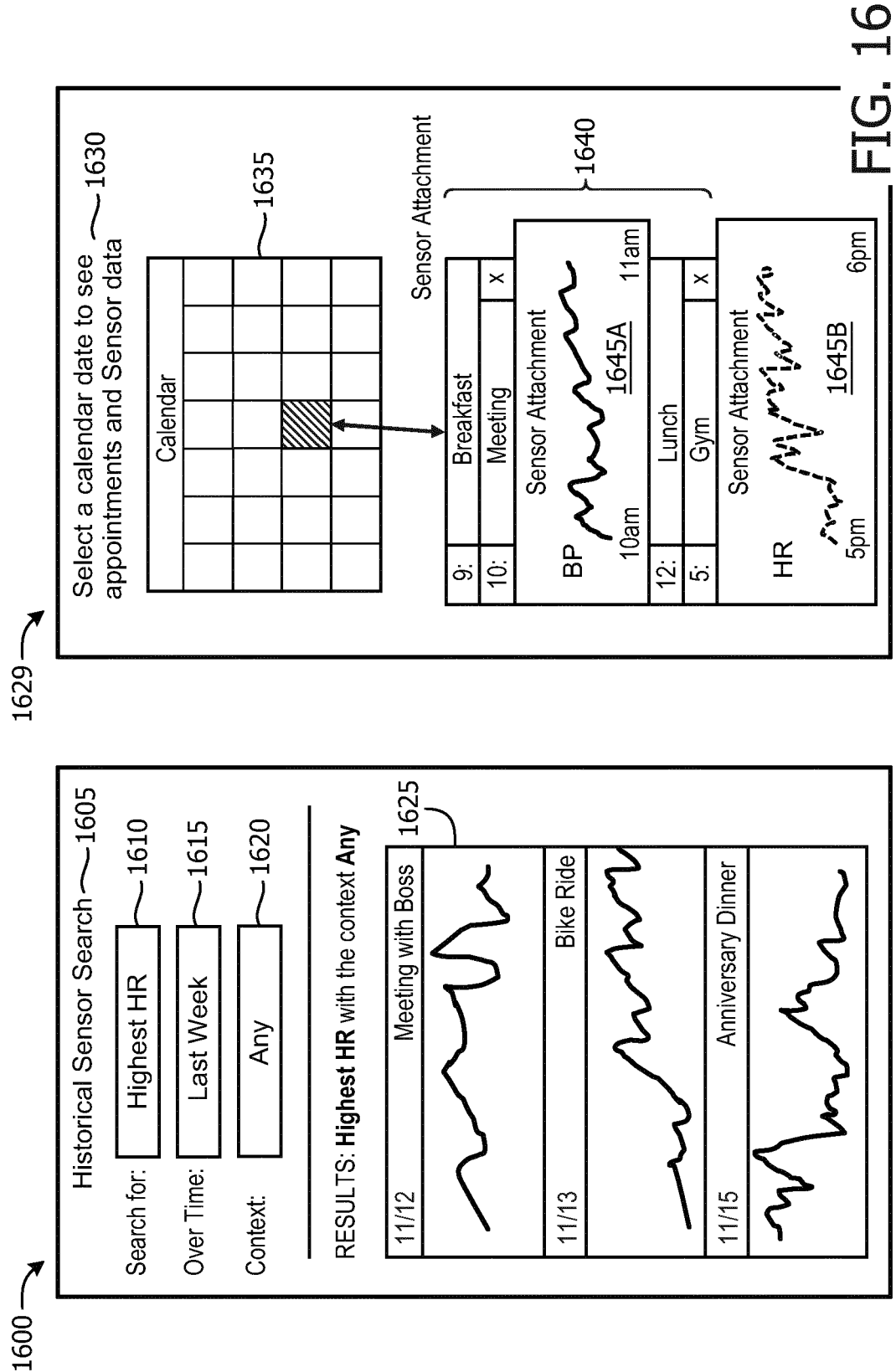

FIGS. 15-16 illustrate example graphical user interfaces in accordance with various embodiments. FIGS. 15-16 each illustrate two different GUIs 1500, 1541 in accordance with the embodiments described herein. A first GUI 1500 is an example context sensor search GUI 1505. The example context sensor search GUI may allow the user to search for historical calendar appointments based upon their sensor data. For example, the GUI in A may include a header identifying that the GUI is for context sensor search that includes the context of work 1515 and excludes the context of exercise 1520. The GUI may also provide features where the user may input terms the user would like to search for or features where the user can include or exclude particular context terms in the search. FIG. 15 includes the particular context term of highest BP 1525 when determining a result that meetings with the boss are associated with a highest blood pressure level 1525 on three different dates 1530 (11/12, 11/15, and 11/20). The context sensor search GUI 1510 also includes a show more results 1535 and a search 1540 selection box. When the search 1540 selection box is selected, the processor at the wearable device may search for events with the highest BP 1510. When the "show more results" 1535 results selection box is selected other data relating to high blood pressure may be displayed on the display at the user device.

The search result provides example blood pressure data that relate to one or more particular appointment types. It may be possible that the GUI may allow the user to search calendar appointments based upon other types of parameters (e.g., vitals parameters) that can trigger an event to be searched.

A second example GUI 1541 may be a context alerts GUI 1545. The context alerts GUI 1545 may show upcoming appointments and provide an alert for the appointments. The alert system may be used to not only tell the user that they have an upcoming appointment but to associate the current appointment with previous appointments and their sensor data.

With the GUI, one may be able to look at appointments similar to the client presentation each with their own associated sensor data. The GUI can also display the last client presentation with corresponding sensor data 1565 (e.g., blood pressure 1570 and heart rate 1575) of the user wearing the wearable device during the last client presentation. By looking at the sensor data, the user may interpret the data and provide/infer conclusions about the condition of the user (e.g., stress) during the appointment.

This example GUI may be useful to alert the user that not only do they have an event coming up, but related vitals data from similar events can inform the user about conditions for the upcoming event.

The context alerts GUI may also include options for the user to see more results, such as a client presentation 1550. If there are more client presentations 1555 and 1560 in the past sensor data may be associated with the context of client presentations 1550, 1555, and 1560. The user may potentially look through their entire calendar of client presentations and see which client presentations triggered what outcomes based on vitals data measured.

FIG. 16 shows some more example graphical user interfaces 1600, 1629. A third GUI 1600, may be a historical sensor data GUI 1605. The historical sensor data GUI 1605 may be similar to the context sensor search GUI 1505, identified as A in FIG. 15, however, the historical sensor data GUI 1605 searches for events using vitals data highest heart rate 1610, over time period "last week" 1615, that corresponds to any context 1620. The historical sensor data GUI 1605 also searches over a time span 1615 as opposed to with a certain context data. Instead of looking for appointments based upon the context data, the historical sensor data GUI 1610 looks for context data based upon a time span 1615.

With the historical sensor data GUI 1605, the user can input particular vitals data the user may be interested in searching for. The user can also provide a time span 1615 over which the search may take place. The GUI may also include a field where the user can filter by context data.

The GUI may then return search results that are viewable in the GUI 1625. For example, as shown in FIG. 16, the search results may include dates of various appointments with corresponding vitals data, such as 11/12, 11/13, and 11/15. In this way, the user can view vitals data for various activities within a period of time.

A fourth example GUI 1629 may be the calendar GUI 1630. The calendar GUI 1630 may be similar to any basic calendar application available. For example the calendar GUI 1630 may show a calendar as a grid of dates 1635 within a given month as would any normal calendar application. A difference may arise, however, when the user selects a particular calendar date. In particular, when the particular calendar date is selected, the calendar GUI as shown in FIG. 16 may not only show the appointments for that date but may also show any available sensor data 1645A and 1645B that may be associated with those calendar appointments 1640.

Figure 17:
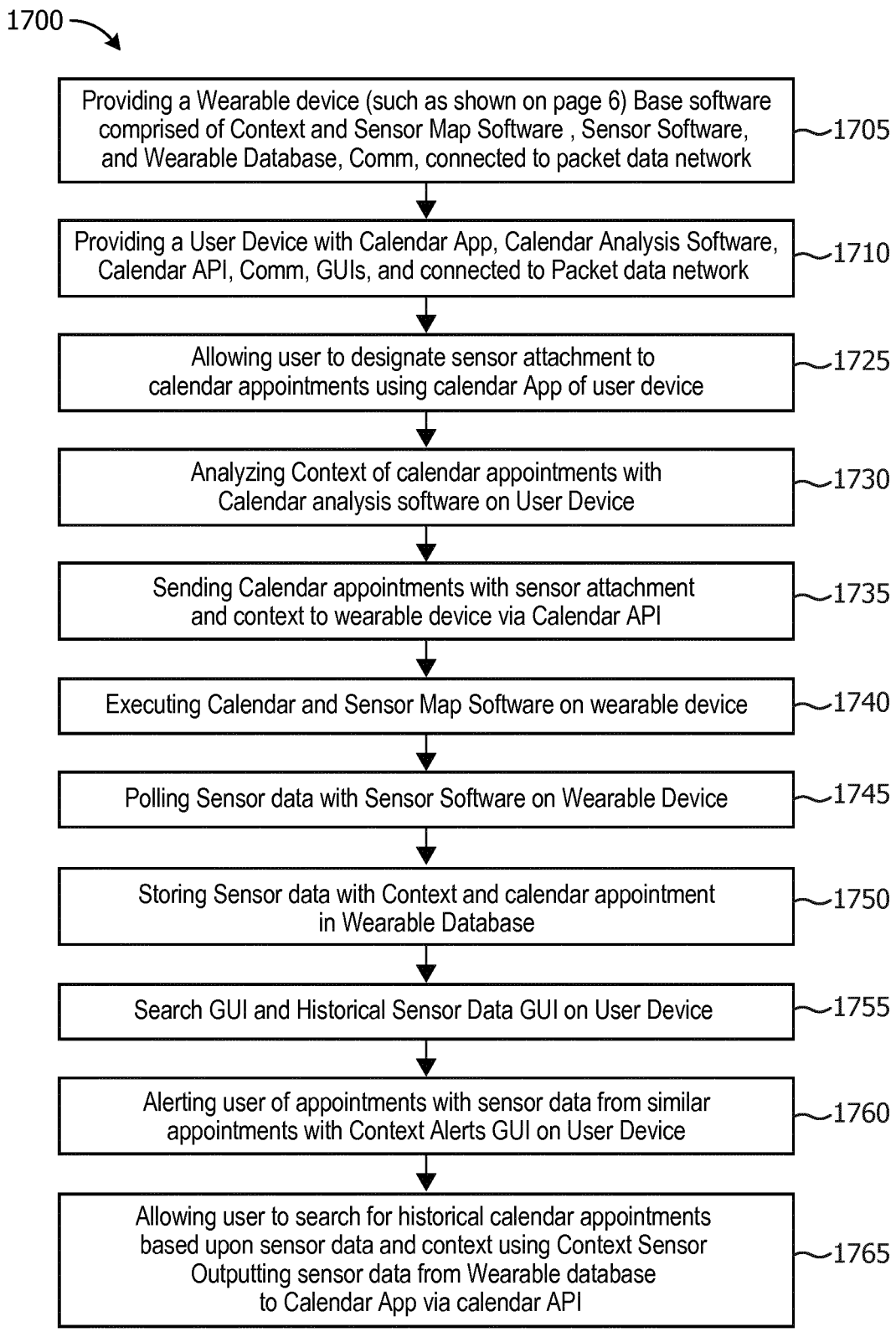
FIG. 17 illustrates an example method for associating wearable devices with calendar contexts in accord with various embodiments.

FIG. 17 illustrates an example method 1700. The method 1700 includes providing a wearable device and a user device as illustrated in FIG. 10.

The wearable device 1005 may be provided, in step 1705, with base instructions 1015 that has context and sensor map instructions 1020 and sensor instructions 1025, wearable database 1035 and communication modules 1010 that connect the wearable device 1005 to the packet data network 1095 in step 1710.

The user device 1040 may be provided with a plurality of applications (e.g., calendar application 1050), application analysis instructions (e.g., calendar analysis instructions 1055), an API 1060, communication module 1045 and plurality of GUI 1065 in step 1710. The user device may also be connected to the packet data network 1095 in step 1710.

The method 1700 includes step 1725 that allows the user to designate sensor data attachments to calendar appointments using the calendar application 1150 of the user device. The method 1700 also includes analyzing context of calendar appointments with calendar analysis instructions 1055 on user device in step 1730. The method 1700 may also send calendar appointments with sensor data attachment and context data to the wearable device using the API 1060 of the user device in step 1735, execute calendar and sensor map instructions 1020 on the wearable device 1005 in step 1740, poll the sensor data with the sensor instructions 1025 on the wearable device 1005 in step 1745, store the sensor data with context data and calendar appointments in the wearable database 1035 in step 1750, allow the user to search for historical calendar appointments based upon sensor data and context using one or more GUI 1065 available on the user device 1040 in step 1755; alerting the user of appointments with sensor data from similar appointments using a GUI on the user device in step 1760, and output sensor data from wearable database to the calendar application using the API of the user device in step 1765.

The various methods may be performed by software, such as, operating in conjunction with hardware. For example, instructions executed by a processor, the instructions otherwise stored in a non-transitory computer readable medium such as a hard disk or flash memory. Various interfaces may be implemented—both communications and interface. One skilled in the art will appreciate the various requisite components of a mobile device and integration of the same with one or more of the foregoing figures and/or descriptions.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for adapting behavior of a wearable device to a user's current context, the method comprising:
   receiving sensor data from at least one sensor of the wearable device;
   comparing the sensor data to a schedule format stored in a memory of the wearable device, wherein the schedule format corresponds to a predetermined scheduled activity and includes at least one characteristic of sensor readings previously associated with the predetermined scheduled activity that comprises:
      a period where a physiological parameter is within a specified range,
      a transition from a low value of the physiological parameter to a high value of the physiological parameter within the specified range, and
      an idle period where the physiological parameter is below the specified range, wherein a first boundary of the idle period indicates a start of the predetermined scheduled activity and a second boundary of the idle period indicates an end of the predetermined scheduled activity;
   determining, based on the received sensor data matching the schedule format, that the user is currently in an identified time of the predetermined scheduled activity;
   identifying an activity for the user to perform associated with the predetermined scheduled activity; and
   instructing the user to perform the activity while the user is in the identified time of the predetermined scheduled activity.

2. The method of claim 1, further comprising:
   activating at least one additional sensor associated with the predetermined scheduled activity, whereby data is collected from the at least one additional sensor while the user is in the predetermined scheduled activity.

3. The method of claim 1, further comprising:
   activating at least one rule associated with the predetermined scheduled activity, whereby while the user is in the predetermined scheduled activity the rule is periodically evaluated against collected sensor data to determine whether the rule is to be applied.

4. The method of claim 1, further comprising:
   suppressing delivery of notifications to the user via a user interface of the wearable device.

5. The method of claim 1, wherein the at least one characteristic belongs to a model that is learned by the wearable device based on previous sensor data and previous user feedback.

6. The method claim 1, further comprising:
   determining that the predetermined scheduled activity is associated with a high stress level for the user; and
   suppressing notifications to the user based on the determinations that the predetermined scheduled activity is associated with a high stress level for the user.

7. The method of claim 1, further comprising:
   receiving physiological data from the at least one sensor, wherein the physiological data comprise one or more of a measure of skin conductance, a measure of blood pressure, a measure of heart rate, a measurement indicating wakefulness, and a measure of skin temperature; and
   storing the received physiological data in association with the predetermined scheduled activity.

8. The method of claim 1, wherein determining that the user is currently in the predetermined scheduled activity comprises matching a current time with the predefined identified time of transition.

9. A wearable device for adapting behavior to a user's current context, the wearable device comprising:
   at least one sensor for receiving sensor data related to a user;
   a memory storing a schedule format corresponding to a predetermined scheduled activity and includes at least one characteristic of sensor readings previously associated with the predetermined scheduled activity comprising:
      a period where a physiological parameter range is within a specified range,
      a transition from a low value of the physiological parameter to a high value of the physiological parameter within the specified range, and
      an idle period where the physiological parameter is below the specified range, wherein a first boundary of the idle period indicates a start of the predetermined scheduled activity and a second boundary of the idle period indicates an end of the predetermined scheduled activity; and
   a processor in communication with the memory and the at least one sensor, the processor being configured to:
      compare the sensor data to the schedule format stored in the memory of the wearable device;
      determine, based on the received sensor data matching the schedule format, that the user is currently in an identified time of the predetermined scheduled activity;
      identify an activity for the user to perform associated with the predetermined scheduled activity; and
      instruct the user to perform the activity while the user is in the identified time of the predetermined scheduled activity.

10. The wearable device of claim 9, wherein the processor is further configured to activate at least one additional sensor associated with the predetermined scheduled activity, whereby data is collected from the at least one additional sensor while the user is in the predefined context.

11. The wearable device of claim 9, wherein the processor is further configured to activate at least one rule associated with the predetermined scheduled activity, whereby while the user is in the predefined context the rule is periodically evaluated against collected sensor data to determine whether the rule is to be applied.

12. The wearable device of claim 9, wherein the processor is further configured to suppress delivery of notifications to the user via a user interface of the wearable device.

13. The wearable device of claim 9, wherein the at least one characteristic belongs to a model that is learned by the wearable device based on previous sensor data and previous user feedback.

14. The wearable device of claim 9, wherein the processor is further configured to:
   determine that the predetermined scheduled activity is associated with a high stress level for the user; and
   suppress notifications to the user based on the determinations that the predetermined scheduled activity is associated with a high stress level for the user.

15. The wearable device of claim 9, wherein the processor is further configured to:
- receive physiological data from the at least one sensor, wherein the physiological data comprise one or more of a measure of skin conductance, a measure of blood pressure, a measure of heart rate, a measurement indicating wakefulness, and a measure of skin temperature; and
- store the received physiological data in association with the predetermined scheduled activity.

16. A non-transitory machine-readable storage medium encoded with instructions for execution by a processor of a wearable device, the non-transitory machine-readable storage medium comprising:
- instructions for receiving sensor data from at least one sensor of the wearable device;
- instructions for comparing the sensor data to a schedule format stored in a memory of the wearable device, wherein the schedule format corresponds to a predetermined scheduled activity and includes at least one characteristic of sensor readings previously associated with the predetermined scheduled activity context comprising;
  - a period where a physiological parameter is within a specified range,
  - a transition from a low value of the physiological parameter to a high value of the physiological parameter within the specified range; and
  - an idle period where the physiological parameter is below the specified range, wherein a first boundary of the idle period indicates a start of the predetermined scheduled activity and a second boundary of the idle period indicates an end of the predetermined scheduled activity;
- instructions for determining, based on the received sensor data matching the schedule format, that the user is currently in an identified time of the predetermined scheduled activity;
- instructions for identifying an activity for the user to perform associated with the predetermined scheduled activity; and
- instructions for instructing the user to perform the activity while the user is in the identified time of the predetermined scheduled activity.

17. The non-transitory machine-readable storage medium of claim 16, further comprising instructions for activating at least one additional sensor associated with the predetermined scheduled activity, whereby data is collected from the at least one additional sensor while the user is in the predetermined scheduled activity.

18. The non-transitory machine-readable storage medium of claim 16, further comprising:
- instructions for determining that the predetermined scheduled activity is associated with a high stress level for the user; and
- instructions for suppressing notifications to the user based on the determinations that the predetermined scheduled activity is associated with a high stress level for the user.

* * * * *